United States Patent [19]
Forte

[11] Patent Number: 5,062,853
[45] Date of Patent: Nov. 5, 1991

[54] BIPOLAR FEMORAL IMPLANT

[76] Inventor: Mark R. Forte, 11 Oak La., Pine Brook, N.J. 07058

[21] Appl. No.: 391,117

[22] Filed: Aug. 8, 1989

[51] Int. Cl.$^5$ .............................................. A61F 2/34
[52] U.S. Cl. .................................................... 623/22
[58] Field of Search ................................... 623/22, 23

[56] References Cited

U.S. PATENT DOCUMENTS

| | | | |
|---|---|---|---|
| 4,380,090 | 4/1983 | Ramos | 623/23 |
| 4,624,674 | 11/1986 | Pappas et al. | 623/22 |
| 4,770,658 | 9/1988 | Geremakis | 623/23 |
| 4,798,610 | 1/1989 | Averill et al. | 623/22 |
| 4,919,674 | 4/1990 | Schelhas | 623/22 |
| 4,936,855 | 6/1990 | Sherman | 623/22 |

FOREIGN PATENT DOCUMENTS

| | | | |
|---|---|---|---|
| 0051686 | 5/1982 | European Pat. Off. | 623/23 |
| 0346270 | 12/1989 | European Pat. Off. | 623/33 |
| 3200340 | 9/1982 | Fed. Rep. of Germany | 623/23 |
| 2583634 | 12/1986 | France | 623/23 |
| 2597329 | 10/1987 | France | 623/33 |

Primary Examiner—Randall L. Green
Assistant Examiner—David H. Willse
Attorney, Agent, or Firm—Klauber & Jackson

[57] ABSTRACT

An implantable prosthetic hip joint includes a spherical acetabular shell articulating within the acetabulum socket of a pelvis and including a spherical shell portion defining an inner spherical surface, and a skirt portion extending downwardly therefrom; a femoral head including a femoral head and a stem secured to the femur of the person; a hemispherical bearing insert mounted in the spherical shell portion for receiving the femoral head for ball-and-socket movement therein; a retractable split annular rim positioned below the bearing insert and including a central opening which permits passage of the femoral head therethrough, and an inner ring surface, the rim including concentric threads along the outer surface thereof which releasably mate with concentric threads along the inner surface of the skirt portion to secure the rim in a first position spaced from the bearing insert and a second position at least substantially in contact with the bearing insert, with an annular recess being defined between the bearing insert and the split rim when the split rim is secured in the first position; and a split spring ring which retains the femoral head in the bearing insert, and includes an annular inner arcuate surface biased into engagement with the femoral head and being movable in the annular recess when the split rim is secured in the first position and being held by the inner ring surface when the split rim is secured in the second position.

39 Claims, 6 Drawing Sheets

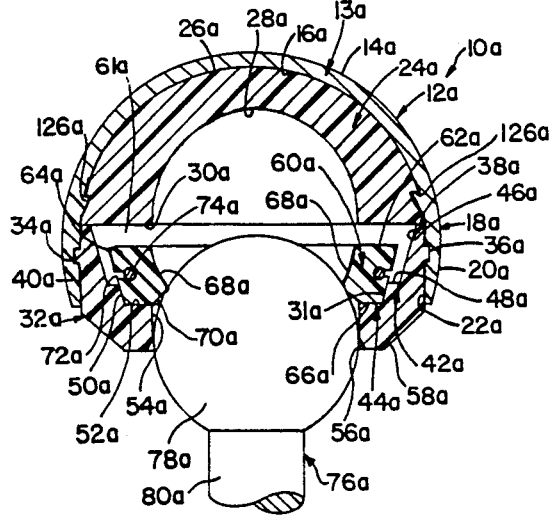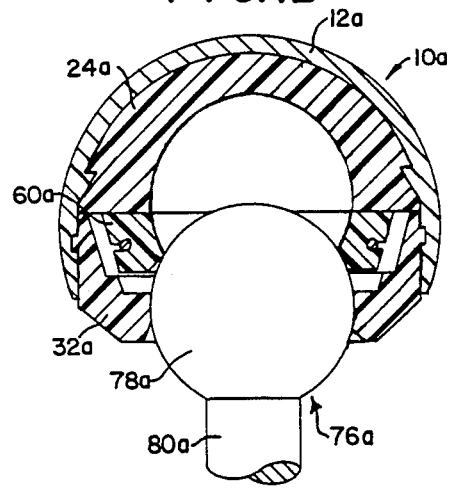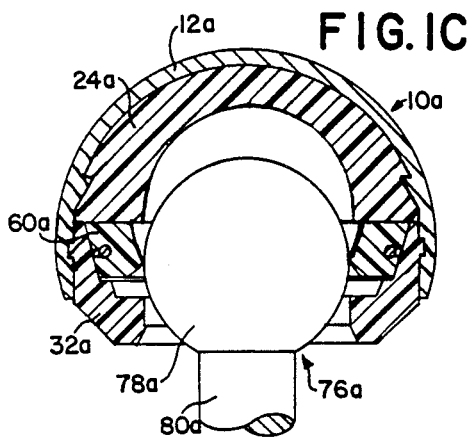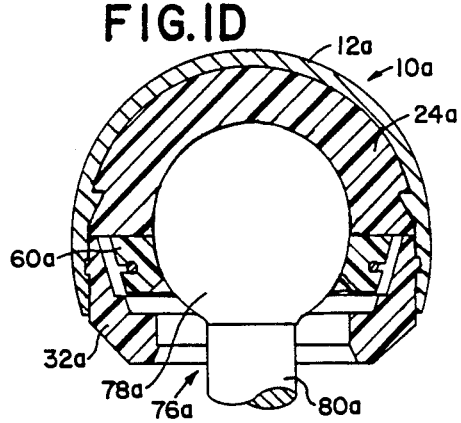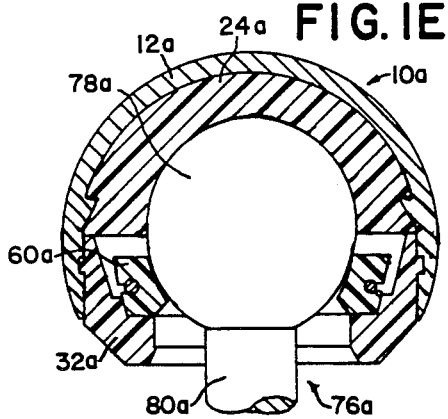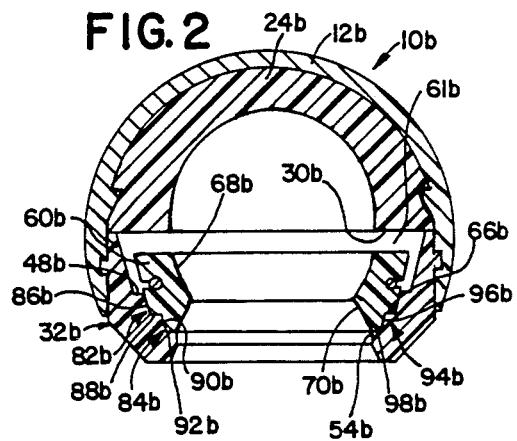

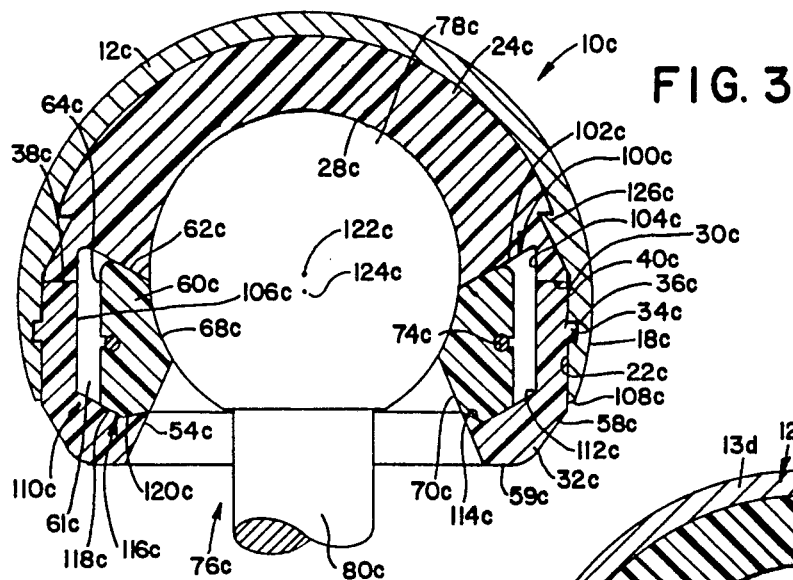
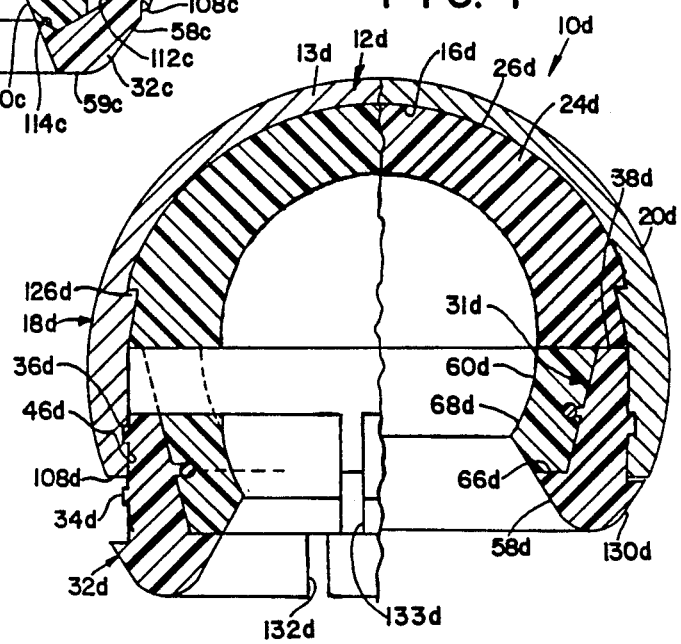
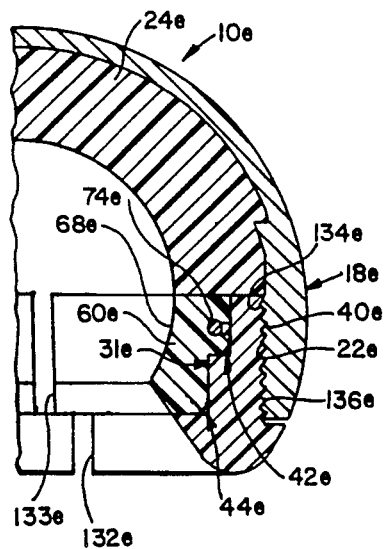
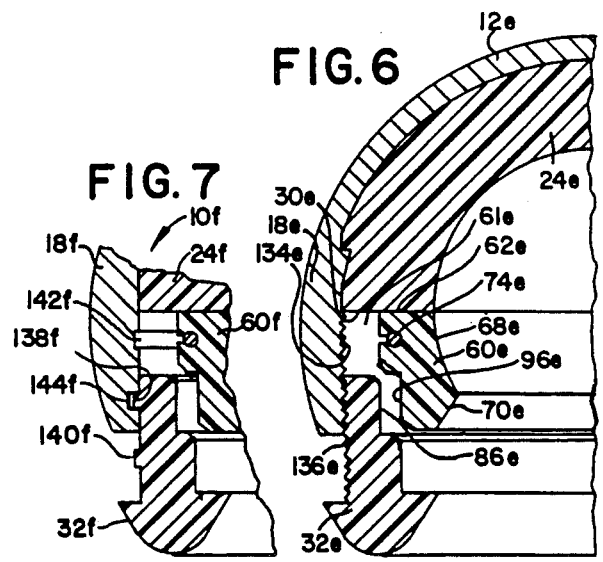

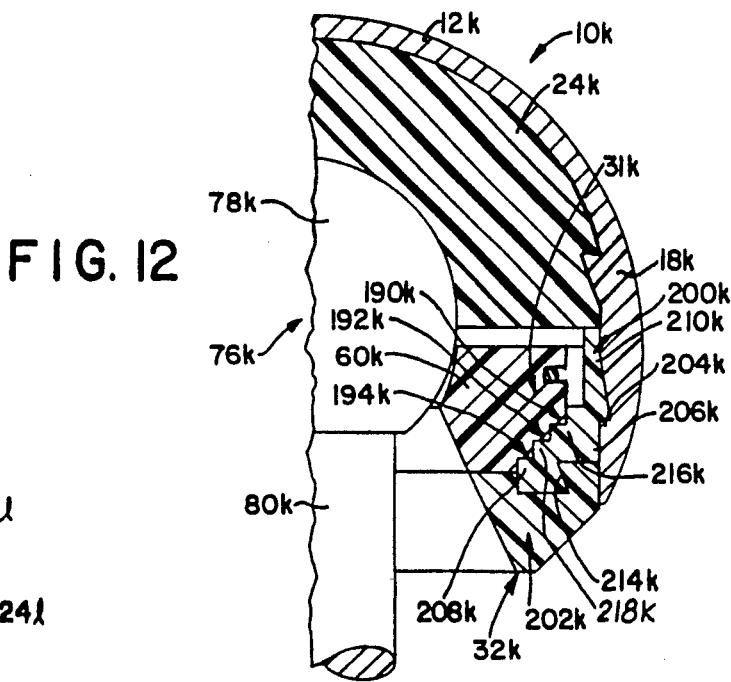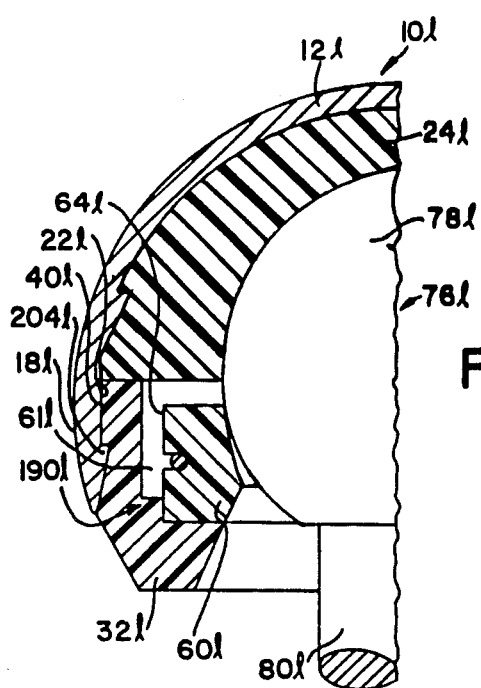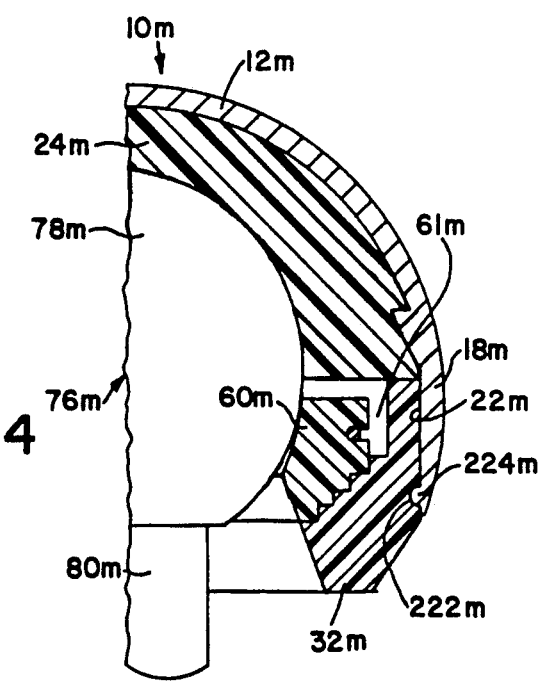

BIPOLAR FEMORAL IMPLANT

BACKGROUND OF THE INVENTION

This invention relates generally to prosthetic devices, and more particularly, to a prosthetic hip joint assembly.

Each hip joint in the human body includes an acetabulum or natural socket in the pelvis which receives the femoral head or ball, which is joined to the femur or thigh bone by a neck portion. As a result, a ball-and-socket joint is provided. In many instances, however, total hip joint replacement may be required. For example, due to various progressive deteriorative diseases, such as osteoarthritis, or abnormal stresses applied to the hip joint, the hip joint, and particularly the femur neck, may fail. In some cases, only the femoral head and neck require replacement, while in other cases, the acetabulum must also be replaced.

Various hip joint prostheses have been proposed. Generally, an acetabular cup is cemented or press fit into the acetabulum socket in the bone. A femoral member comprising an elongated stem, a neck and a head are mounted to the femur by cementing or press fitting the stem into the intramedullary canal of the femur. The femoral head is then received in a bearing insert within the acetabular cup to provide a ball-and-socket movement therein.

In some instances, a bearing insert is provided within the acetabular cup which receives the femoral head, and the acetabular cup articulates within the acetabulum. For example, in U.S. Pat. No. 3,813,699 to Giliberty, a prosthetic hip joint is proposed having an acetabular cup, a bearing insert received in the acetabular cup and a femoral head received in the bearing insert for ball-and-socket movement therein. The bearing insert has a lower open end with a narrowed diameter which defines the entranceway into the interior of the bearing insert. In order to assemble the femoral head in the bearing insert, the femoral head is pressed into the bearing insert such that the reduced diameter open end thereof yields slightly under pressure. After the largest diameter portion of the femoral head passes the reduced diameter opening of the bearing insert, the reduced diameter opening regains its initial shape so as to retain the femoral head therein. However, with such assembly, the femoral head may dislocate and escape from the bearing insert when the leg or body is abnormally twisted. This, of course, requires a new surgical procedure to reinsert the same. Orthopedic prosthetic implant devices of a similar nature are described in U.S. Pat. No. 3,863,273 to Averill; U.S. Pat. No. 4,044,403 to D'Errico; and U.S. Pat. No. 4,408,360 to Keller.

Various other hip prosthetic devices which employ an articulating type of acetabular cup, a bearing insert mounted in the acetabular cup and a femoral head further include a retaining ring secured to the acetabular cup in order to retain the femoral head and bearing insert therein. Examples of such devices are disclosed in U.S. Pat. Nos. 3,818,512 to Shersher; 3,889,299 to Osborne et al.; 4,380,090 to Ramos; and 4,770,661 to Oh. However, with these devices, the retaining ring is inserted after the femoral head is positioned within the bearing insert in the acetabular cup. It will be appreciated, however, that because of the extremely small space at the hip joint, it is difficult to handle such retaining rings. For example, U.S. Pat. No. 3,889,299 to Osborne et al. requires screws to connect the different parts of the retaining ring together. In such case, it would be extremely difficult to insert a screwdriver in such a small space. In U.S. Pat. No. 3,818,512 to Shersher, the retaining ring must be threadedly received within the acetabular cup, and accordingly, a tool must positioned within the hip joint in order to turn the retaining ring a plurality of times in order to secure the same in the acetabular cup, which is extremely difficult in the small space. In U.S. Pat. No. 4,380,090 to Ramos, a thin locking ring must be positioned within a narrow groove in the acetabular cup, which again is extremely difficult to manipulate with such a thin locking ring. Finally, in U.S. Pat. No. 4,770,661 to Oh, the retaining ring is comprised of two separate parts, and therefore additional space must be provided for securing the two parts together at the hip joint.

In U.S. Pat. No. 4,241,463 to Khovaylo, there is disclosed a prosthetic implant device for a hip joint. In this case, the bearing insert is provided with an upwardly and outwardly inclined inner, annular wall. A split ring is positioned within the recess provided thereby so that, as the femoral head is inserted into the bearing insert, the split ring moves up the inclined wall and moves apart to permit the femoral head to enter the inner dome of the bearing insert, whereupon the split ring falls back down. If a pulling force is applied to the femoral head to remove the same, for example, during an abnormal twisting or torquing movement, a wedging effect takes place with respect to the split ring to prevent removal of the femoral head. In actual practice, however, such an assembly has proven unsatisfactory since the wedging effect does not completely prevent removal of the femoral head. As a result, in the actual commercial models of the Khovaylo device, the bearing insert has been provided with an inner, annular ledge which more positively prevents the split ring from escaping, even when the pulling force on the femoral head is great. However, with Khovaylo, because of the large space required for sliding of the split ring during insertion of the femoral head, the dimensions of the split locking ring must be made smaller. Accordingly, there is less bearing contact of the split ring with the femoral head when the latter is inserted within the bearing insert, and less contact area at the opposite surface of the split ring with the wedging, locking surface, thereby permitting easier escape of the femoral head from the bearing insert. In addition, because of this movement, and the strength requirements that are necessary on the smaller split ring, there is a restriction on the types of materials that can be used to construct the same. Of a similar nature is U.S. Pat. No. 3,862,807 to Doden, which has even less contact of the split ring with the ball shaped member, that is, in which there is only an effective line contact when the femoral head is inserted within the bearing insert. This is due to the rectangular cross-section of the bearing insert.

U.S. Pat. No. 3,787,128 to Maistrelli discloses a device in which a split retaining ring is inserted after the ball is inserted within the socket, and would therefore suffer from the same problems as Khovaylo.

U.S. Pat. No. 3,683,421 to Martinie discloses a prosthetic joint assembly which is much less relevant than the above references, but which is included herein for a complete review of the prior art.

OBJECTS AND SUMMARY OF THE INVENTION

Accordingly, it is an object of the present invention to provide an implantable prosthetic joint that overcomes the aforementioned problems with the prior art.

It is another object of the present invention to provide an implantable prosthetic joint in which insertion of the femoral head in the bearing insert is accomplished by a mere push of the femoral head therein.

It is yet another object of the present invention to provide an implantable prosthetic joint in which the split lock ring can be constructed with dimensions larger than that of the prior art.

It is a further object of the present invention to provide an implantable prosthetic joint with an increased surface area of contact between the split lock ring and the femoral head, and the wedging locking surfaces at the opposite outer side of the split ring.

It is still a further object of the present invention to provide an implantable prosthetic joint in which the level of security, relative to the forces required to produce premature escape of the femoral head, is increased.

It is yet a further object of the present invention to provide an implantable prosthetic joint in which the design of the bearing insert facilitates use of different bearing materials.

It is another object of the present invention to provide an implantable prosthetic joint which permits easy removal of the femoral head from the bearing insert by a surgeon, when removal or revision of the prosthetic device is required.

In accordance with an aspect of the present invention, an implantable prosthetic joint includes first bone securing means for constraining the prosthetic joint within a first bone of a biological joint, the first bone securing means including a spherical shell articulating within a socket in the first bone, the shell including an inner spherical surface and an open circumferential end; second bone securing means for securing the prosthetic joint in a second bone of the biological joint, the second bone securing means including a femoral head and stem means connected with the femoral head for securing the prosthetic joint to the second bone; bearing means for connecting the second bone securing means with the first bone securing means, the bearing means including an outer spherical dome which engages with the inner spherical surface of the shell, an open circumferential end, ah inner spherical surface which receives the femoral head for ball-and-socket movement therein, and an inner annular surface at the open circumferential end, the inner annular surface including at least one annular step; and split spring ring means for retaining the femoral head in the bearing means, the split spring ring means including an annular inner engaging surface biased into engagement with the femoral head when the femoral head is seated in the bearing means, and the split spring ring means engaged with the at least one annular step of the inner annular surface when said femoral head is fit within said bearing means.

In accordance with another aspect of the present invention, an implantable prosthetic joint includes first bone securing means for constraining the prosthetic joint within a first bone of a biological joint, the first bone securing means including a spherical shell articulating within a socket in the first bone, the shell including an inner spherical surface and an open circumferential end; second bone securing means for securing the prosthetic joint to a second bone of the biological joint, the second bone securing means including a femoral head and stem means connected with the femoral head for securing the prosthetic joint to the second bone; bearing means for connecting the second bone securing means with the first bone securing means, the bearing means including an open circumferential end, an outer spherical dome which engages with the inner spherical surface of the shell, an inner spherical surface which receives the femoral head for ball-and-socket movement therein, and an annular recess in the inner spherical surface, the annular recess being defined by an upper annular inclined wall and a lower annular inclined wall, the upper and lower annular inclined walls being inclined upwardly away from the open circumferential end; and split spring ring means for retaining the femoral head in the bearing means, the split spring ring means including an inner engaging surface biased into engagement with the femoral head when the femoral head is seated in the bearing means, the split spring ring means being slidably positioned in the recess and including an upper annular inclined surface and a lower annular inclined surface, the upper and lower annular inclined surfaces being inclined upwardly away from the open circumferential end, and the distance between the upper and lower annular surfaces being only slightly smaller than the distance between the upper and lower annular walls.

In accordance with still another aspect of the present invention, an implantable prosthetic joint includes first bone securing means for constraining the prosthetic joint within a first bone of a biological joint, the first bone securing means including a spherical shell articulating within a socket in the first bone, the shell including an inner spherical surface and an open circumferential end; second bone securing means for securing the prosthetic joint to a second bone of the biological joint, the second bone securing means including a femoral head and stem means connected with the femoral head for securing the prosthetic joint to the second bone; bearing means for connecting the second bone securing means with the first bone securing means, the bearing means including a bearing insert having an outer spherical dome which engages with the inner spherical surface of the shell and an inner spherical surface which receives the femoral head for ball-and-socket movement therein, and a retractable annular split rim positioned below the bearing insert and including a central opening which permits passage of the femoral head therethrough and an inner ring surface, the retractable split rim including securing means for releasably securing the split rim in a first position spaced from the bearing insert and a second position at least substantially in contact with the bearing insert, an annular recess being defined between the bearing insert and the split rim when the split rim is secured in the first position; and split spring ring means for retaining the femoral head in the bearing means, the split spring ring means including an annular inner engaging surface biased into engagement with the femoral head and being positioned between the bearing insert and the retractable split rim, the split spring ring means being movable in the annular recess when the split rim is secured in the first position and being held by the inner ring surface when the split rim is secured in the second position.

In accordance with yet another aspect of the present invention, an implantable prosthetic joint includes first bone securing means for constraining the prosthetic joint within a first bone of a biological joint, the first bone securing means including a spherical shell articulating within a socket in the first bone, the shell including an inner spherical surface and an open circumferential end; second bone securing means for securing the prosthetic joint to a second bone of the biological joint, the second bone securing means including a femoral head and stem means connected with the femoral head for securing the prosthetic joint to the second bone; bearing means for connecting the second bone securing means with the first bone securing means, the bearing means including a bearing insert having an outer shell dome which engages with the inner spherical surface of the shell and an inner spherical surface which receives the femoral head for ball-and-socket movement therein, and an insert rim positioned below the bearing insert, the insert rim including an open circumferential end, an upper surface spaced from the bearing insert to define a guideway, and an inner annular ring surface, an annular recess being defined between the bearing insert and the inner ring surface of the insert rim, the inner ring surface including a lower ledge; and split spring ring means for retaining the femoral head in the bearing means, the split spring ring means including an upper split lock ring section having a sliding section slidable within the guideway and an inner engaging surface biased into engagement with the femoral head when the femoral head is seated in the bearing means, and a lower split lock ring section positioned for movement in the annular recess and engageable with the lower ledge of the inner ring surface when a pulling force is exerted between the first and second bone securing means to prevent removal of the femoral head from the bearing means.

The above and other objects, features and advantages of the present invention will become readily apparent from the following detailed description thereof which is to be read in connection with the accompanying drawings.

BRIEF DESCRIPTION OF THE DRAWINGS

FIG. 1A is a cross-sectional view of an implantable prosthetic joint according to a first embodiment of the present invention with the femoral head unassembled therewith;

FIG. 1B is a cross-sectional view of the implantable prosthetic joint of FIG. 1A, showing insertion of the femoral head at a first intermediate position therein;

FIG. 1C is a cross-sectional view of the implantable prosthetic joint of FIG. 1A, showing the femoral head inserted to a further extent;

FIG. 1D is a cross-sectional view of the implantable prosthetic joint of FIG. 1A, showing the femoral head fully inserted within the bearing insert and with the split lock ring at its uppermost position;

FIG. 1E is a cross-sectional view showing the final position of the implantable prosthetic joint of FIG. 1A;

FIG. 2 is a cross-sectional view of an implantable prosthetic joint according to another embodiment of the present invention;

FIG. 3 is a cross-sectional view of an implantable prosthetic joint according to another embodiment of the present invention;

FIG. 4 is a cross-sectional view of an implantable prosthetic joint according to another embodiment of the present invention, the left side showing the position of the retaining ring and the retractable rim prior to insertion of the femoral head and the right side showing the final position thereof after insertion of the femoral head in the bearing insert and final locked contraction of the rim;

FIG. 5 is a cross-sectional view of a portion of an implantable prosthetic joint according to another embodiment of the present invention;

FIG. 6 is a cross-sectional view of a portion of the implantable prosthetic joint of FIG. 5, in order to explain the operation thereof;

FIG. 7 is a cross-sectional view of a portion of an implantable prosthetic joint according to another embodiment of the present invention;

FIG. 12 is a cross-sectional view of a portion of an implantable prosthetic joint according to another embodiment of the present invention;

FIG. 13 is a cross-sectional view of a portion of an implantable prosthetic joint according to another embodiment of the present invention;

FIG. 14 is a cross-sectional view of a portion of an implantable prosthetic joint according to another embodiment of the present invention;

DETAILED DESCRIPTION OF THE PREFERRED EMBODIMENTS

Figure 8A:
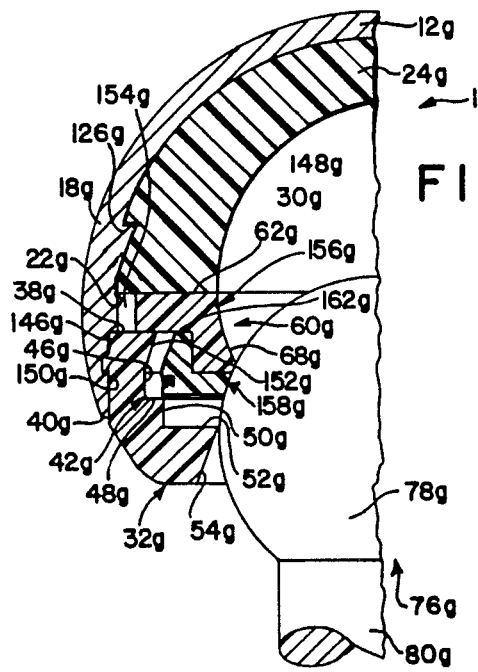
FIG. 8A is a cross-sectional view of a portion of an implantable prosthetic joint according to another embodiment of the present invention, with the femoral head unassembled therewith.

Referring to the drawings in detail, an implantable prosthetic joint according to the present invention will now be described, such implantable prosthetic joints generally being of the type described in U.S. Pat. No. 4,241,463 to Khovaylo, the entire disclosure of which is incorporated herein by reference.

Referring first to FIG. 1A, an implantable prosthetic joint 10a according to a first embodiment of the present invention, includes an acetabular shell or cup 12a which articulates within the acetabulum socket (not shown) of the pelvis. Preferably, acetabular shell 12a is formed by a substantially hemispherical shell portion 13a having an outer spherical surface 14a and an inner spherical surface 16a. Acetabular shell 12a further includes a spherical skirt portion 18a formed at the free end of hemispherical shell portion 13a. Skirt portion 18a includes an outer substantially spherical surface 20a and an inner substantially cylindrical surface 22a, with outer surface 20a being continuous with outer surface 14a, and inner surface 22a being continuous with inner surface 16a. Preferably, acetabular shell 12a transitions from substantially hemispherical shell portion 13a to skirt portion 18a at or about the level of the transverse diametrical plane through the center of the femoral head seated in implantable prosthetic joint 10a. The reason for this transition from inner surface 16a of substantially hemispherical shell portion 13a to inner surface 22a of skirt portion 18a is to provide access for assembly of the bearing insert and insert rim according to the present invention, as will be described in greater detail hereinafter. Preferably, acetabular shell 12a has a wall thickness in the range of approximately 2-3 mm, and outer surfaces 14a and 20a are highly polished to minimize frictional torque when acetabular shell 12a is articulating with the biological surface of the acetabulum or hip socket.

Acetabular shell 12a is fabricated from a material which is sufficient to withstand forces such as impact, wear and abrasion, during use. Further, such material must be compatible with bone and body tissues of the patient to which acetabular shell 12a is implanted. In this regard, suitable materials include metallic alloys such as cobalt-chrome-molybdenum alloys, titanium alloys and stainless steel alloys, as well as ceramic compositions.

Implantable prosthetic joint 10a further includes a bearing insert 24a which seats within acetabular shell 12a. Specifically, bearing insert 24a has a substantially hemispherical configuration with an outer substantially hemispherical domed surface 26a of substantially identical shape and dimensions as inner spherical surface 16a so as to matingly engage therewith.

A plurality, for example, three or four, of equiangularly spaced ribs, keys, barbs or the like 126a may be formed on inner spherical surface 16a near the transition with inner surface 22a of skirt portion 18a. In this manner, bearing insert 24a is made of a deformable plastic material and is forcibly inserted into acetabular shell 12a, barbs 126a will cut into bearing insert 24a, whereby plastic flow will occur so that bearing insert 24a is restrained in acetabular shell 12a from pull-out and rotation. Of course, where bearing insert 24a is made from a ceramic material, other securing means are provided, such as that described below with respect to rib 34a and groove 36a, incorporated into bearing insert 24a and shell 12a, respectively.

In addition, bearing insert 24a includes an inner substantially hemispherical bearing surface 28a. Bearing insert 24a is dimensioned to accommodate the femoral head for ball-and-socket movement therein. In this regard, bearing insert 24a is preferably fabricated from a molded or machined ultra-high molecular-weight polyethylene (UHMWPE), aluminum oxide, zirconium oxide ceramic or other comparable material.

It will be appreciated that in this first embodiment, the annular outer face 30a of bearing insert 24a has a planar configuration.

Implantable prosthetic joint 10a further includes an annular insert rim 32a which is locked to the inner cylindrical surface 22a of skirt portion 18a at a position below bearing insert 24a and in contact with outer face 30a thereof so as to lock bearing insert 24a in the position shown in FIG. 1A. The manner of locking insert rim 32a to acetabular shell 12a can take different forms, such as an outer circumferential rib 34a on insert rim 32a which fits within a circumferential groove 36a in inner cylindrical surface 22a of skirt portion 18a. However, any other suitable means for locking insert rim 32a to acetabular shell 12a can be used, such as barbs or the like, and other locking means will be described hereinafter with respect to other embodiments of the present invention. Insert rim 32a is preferably fabricated of UHMWPE.

As shown in FIG. 1A, insert rim 32a includes an annular substantially planar upper surface 38a in abutting contact with annular outer face 30a of bearing insert 24a. It will be appreciated, however, that the wall thickness of insert rim 32a at upper surface 38a thereof is much smaller than the wall thickness of bearing insert 24a at outer face 30a thereof. Insert rim 32a has an outer substantially cylindrical surface 40a having an outer diameter substantially identical to the inner diameter of inner surface 22a of skirt portion 18a.

The inner ring surface 31a of insert rim 32a is stepped so as to include an annular upper step 42a and an annular lower step 44a. Specifically, upper step 42a is formed by an annular inclined inner wall surface 46a which is inclined in a converging manner from the inner edge of planar upper surface 38a, and which terminates in an annular horizontal inwardly extending ledge 48a which also forms part of upper step 42a. In like manner, lower step 44a includes an annular inclined inner wall surface 50a which converges downwardly from the inner end of horizontal ledge 48a and which terminates in an annular horizontal inwardly extending ledge 52a which forms part of lower step 44a.

From the inner circumferential edge of horizontal ledge 52a, an inner cylindrical wall surface 54a is provided and defines an opening for insertion of the femoral head within bearing insert 24a. In this regard, the lower portion of cylindrical wall surface 54a is provided with an annular bevel 56a to facilitate smooth entry of the femoral head within bearing insert 24a.

It will further be appreciated that insert rim 32a includes a frusto-conical outer wall 58a which extends in a converging direction from the lower end of outer cylindrical surface 40a of insert rim 32a. In this manner, frusto-conical outer wall 58a of insert rim 32a is within the projected outer spherical surface 20a of acetabular shell 12a to present a smooth transition to the soft tissues of the acetabulum.

It will be appreciated that, although bearing insert 24a and insert rim 32a have been shown as two separate components, insert rim 32a can be fabricated integrally with bearing insert 24a. In this regard, reference to bearing means through the description and claims of the present application will refer to the combination of bearing insert 24a and insert rim 32a.

A split lock ring 60a is provided in the annular recess 61a defined by outer face 30a of bearing insert 24a and the inner ring surface 31a of insert rim 32a defined by upper and lower steps 42a and 44a and inclined inner wall surface 46a. Split lock ring 60a includes an annular upper planar surface 62a adapted to abut against outer face 30a of bearing insert 24a during insertion of the femoral head into bearing insert 24a. In addition, split lock ring 60a includes an outer annular inclined surface 64a having an inclination substantially identical to annular inclined inner wall surfaces 46a and 50a of upper and lower steps 42a and 44a, respectively, so as to mate therewith. Split lock ring 60a further includes an annular lower planar surface 66a adapted to seat on either horizontal ledge 48a or horizontal ledge 52a. In this regard, it will be appreciated that the height of split lock ring 60a, measured between upper and lower planar surfaces 62a and 66a, is only slightly less than the distance between outer face 30a of bearing insert 24a and upper horizontal ledge 48a. In this manner, when upper planar surface 62a is biased into abutting relation with outer face 30a of bearing insert 24a, split lock ring 60a can then be slid outwardly along outer face 30a until outer inclined surface 64a is in contact, and thereby limited by, inclined inner wall surface 46a of insert rim 32a.

In addition, split lock ring 60a includes an inner annular inclined surface 68a, which preferably is an arcuate surface, such that when split lock ring 60a is seated on lower horizontal ledge 52a and in contact with inclined inner wall surface 50a of insert rim 32a, inner surface 68a is formed along nearly the same sphere of inner substantially hemispherical bearing surface 28a of bearing insert 24a so as to increase the effective bearing contact area with the femoral head, while locking the same in position. It is noted that surface 68a need not be arcuate, but can, for example, be frusto-conical.

In order to permit easier access of the femoral head into bearing insert 24a, the lower portion of inner inclined surface 68a of split ring lock 60a is beveled outwardly, as at 70a.

Split lock ring 60a is preferably fabricated from an ultra high molecular weight polyethylene (UHMWPE) or a ceramic composite material. In this regard, split lock ring 60a preferably has some elasticity and resilience such that it can be expanded outwardly and, upon release of the external outwardly expanding force, split lock ring 60a will return to its initial configuration and restore to its seated position within insert rim 32a. Alternatively, or in addition thereto, split lock ring 60a can be provided with a circumferential groove 72a along outer inclined surface 64a thereof, which receives a spring rod 74a that functions to bias split lock ring 60a to a compressed position, and thereby positively return split lock ring 60a to its compressed condition upon the removal of the external outwardly directed force thereon.

As used in the present application, the term "split spring ring means" is intended to constitute either an elastic, resilient split lock ring 60a and/or the combination of split lock ring 60a with spring rod 74a.

Finally, implantable prosthetic joint 10 includes a femoral component 76a having a ball-shaped femoral head 78a and a femoral neck 80a extending therefrom, with the free end of femoral neck 80a being connected with a femoral stem (not shown) which is connected with the femur of a person.

In operation, femoral head 78a is inserted through the open end of insert rim 32a, that is, through the circular space defined by inner cylindrical wall surface 54a of insert rim 32a, until femoral head 78a thereof contacts beveled surface 70a of split lock ring 60a. Further advancement of femoral head 78a results in movement of split lock ring 60a vertically upward in FIG. 1A until upper planar surface 62a of split lock ring 60a abuts against outer face 30a of bearing insert 24a, without outward expansion of split lock ring 60a. Thereafter, further advancement of femoral head 78a results in femoral head 78a biasing split lock ring 60a apart, that is, in the outward direction, as shown in FIG. 1C, until outer inclined surface 64a of split lock ring 60a abuts against inclined inner wall surface 46a of insert rim 32a. Upon continued advancement such that femoral head 78a advances past split lock ring 60a, as shown in FIG. 1D, spring rod 74a biases split lock ring 60a back to its contracted position. In such position, inner inclined arcuate surface 68a of split lock ring 60a contacts the outer surface of femoral head 78a and then rides down such surface until split lock ring 60a seats on horizontal ledge 52a of lower step 44a, as shown in FIG. 1E. As a result, femoral head 78a is locked within bearing insert 24a for ball-and-socket movement therein. This is because split lock ring 60a is retained on lower step 44a to prevent accidental removal of femoral head 78a therefrom. At the same time, the inner inclined surface 68a of split lock ring 60a provides an effective extension of the inner substantially hemispherical bearing surface 28a of bearing insert 24a.

It will be appreciated that the provision of upper and lower steps 42a and 44a according to the present invention enables the use of a split lock ring 60a of larger dimensions than that achieved with U.S. Pat. No. 4,241,463 to Khovaylo, thereby providing greater femoral head 78a overlap. This improves the level of security relative to the torque and axial force required to provide premature escape of femoral head 78a from bearing insert 24a.

Further, with the arrangement of FIGS. 1A–1E, and particularly that of bearing insert 24a with insert rim 32a, use of different bearing materials is facilitated, and also reducing the cost and complexity of construction. For example, because of such two-piece construction of bearing insert 24a with insert rim 32a, bearing insert 24a can be made of a ceramic material, while insert rim 32a can be made of a plastic material. This enables insert rim 32a to be readily machined for fine corners, while providing a more durable bearing surface of bearing insert 24a.

Further, a bail-out mode is provided for easy removal of femoral head 78a from bearing insert 24a by a surgeon. Specifically, to disassemble femoral head 78a from bearing insert 24a, a hemostat or similar instrument (not shown) is inserted in the gap between insert rim 32a and femoral head 78a to displace split lock ring 60a upwardly to the position shown in FIG. 1D. With the hemostat or other instrument maintaining split lock ring 60a in the upper position shown in FIG. 1D, femoral head 78a is pulled downwardly, whereby split lock ring 60a expands to the position shown in FIG. 1C. Then, the hemostat or other instrument is removed, and upon continued removal of femoral head 78a, split lock ring 60a assumes the sequential positions shown in FIGS. 1B and 1A.

Referring now to FIG. 2, an implantable prosthetic joint 10b according to another embodiment of the present invention will now be described, in which elements corresponding to those described above with respect to implantable prosthetic joint 10a are identified by the same reference numerals, with the exception that the letter "a" is replaced by the letter "b" following the respective numeral. A detailed description of the identical elements will be omitted herein for the sake of brevity. Specifically, acetabular shell 12b, bearing insert 24b and the femoral head (not shown) are identical to the corresponding elements of implantable prosthetic joint 10a of FIGS. 1A–1E.

However, insert rim 32b differs from insert rim 32a in that lower step 44a of insert rim 32a is replaced by an annular intermediate step 82b and an annular lower step 84b. In this regard, intermediate step 82b extends downwardly from the inner edge of horizontal ledge 48b. Specifically, intermediate step 82b includes a frusto-conical inclined inner wall surface 86b that extends downwardly in a converging manner from the inner edge of horizontal ledge 48b. Intermediate step 82b further includes a horizontal annular ledge 88b which extends inwardly from the lower end of inclined inner wall surface 86b. In like manner, lower step 84b includes a frusto-conical inclined inner wall surface 90b extending downwardly in a converging manner from the inner end of horizontal ledge 88b, and a lower horizontal annular ledge 92b extending inwardly from inclined inner wall surface 90b. Inner cylindrical wall surface 54b extends downwardly from the inner edge of horizontal ledge 92b. The remainder of insert rim 32b is identical to insert rim 32a.

In correspondence with this change in insert rim 32b, split lock ring 60b includes a step extension 94b. Specifically, lower annular planar surface 66b extends inwardly a small distance and terminates in a downwardly extending frusto-conical inclined annular wall 96b that extends downwardly in a converging manner and which terminates in a lower annular planar surface 98b. Because of extension 94b, beveled surface 70b extends downwardly at a greater angle than beveled surface 70a and terminates at the inner edge of lower annular planar surface 98b.

It will be appreciated that the widthwise dimensions of lower planar surface 66b, lower planar surface 98b, horizontal ledge 88b and horizontal ledge 92b are all substantially identical. Thus, when split lock ring 60b is in the position shown in FIG. 2, beveled surface 70b thereof forms a substantially continuous inclined extension of inner cylindrical wall surface 54b of insert rim 32b.

In the embodiment of FIG. 2, it will be appreciated that the distance between outer face 30b of bearing insert 24b and horizontal ledge 48b is substantially identical to the distance between outer face 30a and horizontal ledge 48a in the embodiment of FIGS. 1A–1E. However, by providing an additional step of FIG. 2, inner inclined arcuate bearing surface 68b of split lock ring 60b can be made larger so as to engage a larger area of the femoral head and a larger area of contact of the locking surfaces, so as to improve the level of security relative to the forces required to produce premature escape of the femoral head in situ.

Referring now to FIG. 3, an implantable prosthetic joint 10c according to another embodiment of the present invention will now be described in which elements corresponding to those in the implantable prosthetic joint 10a of FIGS. 1A–1E are identified by the same reference numerals, with the exception that the letter "c" is appended to each numeral, and a detailed description of the common elements is omitted herein for the sake of brevity.

As shown, acetabular shell 12c and femoral head 78c are identical to corresponding elements of implantable prosthetic joint 10a.

Bearing insert 24c differs from bearing insert 24a at the outer face 30c thereof. Specifically, the inner portion of outer face 30c is cut away to provide a substantially triangular cross-sectional recess 100c defined by an annular superior guide surface 102c that extends outwardly and upwardly in FIG. 3 from the free edge of inner substantially hemispherical bearing surface 28c of bearing insert 24c, and which terminates at the upper end of a downwardly extending cylindrical surface 104c, the lower end of downwardly extending cylindrical surface 104c meeting the inner end of outer face 30c. It will be appreciated that the width of outer face 30c is substantially identical to the width of insert rim 32c at upper planar surface 38c thereof. In other respects, bearing insert 24c is similar to bearing insert 24a of implantable prosthetic joint 10a shown in FIGS. 1A–1E.

Insert rim 32c includes an outer cylindrical surface 40c having an outer diameter substantially identical to the inner diameter of inner cylindrical surface 22c of skirt portion 18c of acetabular shell 12c. In addition, inner cylindrical surface 22c is formed with a circumferential groove 36c which receives an annular rib 34c formed on the outer cylindrical surface 40c of insert rim 32c so as to releasably lock insert rim 32c to acetabular shell 12c in the same manner discussed above with respect to insert rim 32a of implantable prosthetic joint 10a.

In the same manner as insert rim 32a, insert rim 32c includes an inclined frusto-conical outer wall 58c which converges downwardly from the lower end of outer cylindrical surface 40c and which terminates in a lower annular horizontal planar surface 59c.

Insert rim 32c differs from insert rim 32a by providing an inner frusto-conical wall surface 54c in place of inner cylindrical wall 54a of insert rim 32a. Frustoconical wall surface 54c extends upwardly toward bearing insert 24c from the inner edge of lower horizontal planar surface 59c in a converging manner.

In addition, insert rim 32c does not include any steps, such as steps 42a and 44a of insert rim 32a. Rather, insert rim 32c includes an inner cylindrical wall 106c that extends downwardly from the inner edge of planar upper surface 38c thereof. It will therefore be appreciated that cylindrical wall 106c effectively forms a continuation of downwardly extending cylindrical surface 104c of bearing insert 24c. In this regard, it is noted that the lower end of cylindrical wall 106c extends down to a position adjacent to the lower free end 108c of acetabular shell 12c.

A concave substantially V-shaped annular surface 110c connects the lower end of cylindrical wall 106c with the upper end of frusto-conical wall surface 54c. Specifically, V-shaped annular surface 110c includes a first frusto-conical annular surface 112c that extends inwardly and downwardly in a converging manner from the lower end of cylindrical wall 106c and a second frusto-conical annular surface 114c that extends upwardly and inwardly in a converging manner from the inner edge of frusto-conical annular surface 112c and which terminates at the upper edge of frusto-conical wall surface 54c. It will be appreciated that the widthwise dimension of frusto-conical annular surface 112c is greater than that of frusto-conical annular surface 114c and, in fact, is approximately twice the width thereof. In this manner, frusto-conical annular surface 112c functions as a ramping surface and locking surface, while frusto-conical annular surface 114c functions as a constraining surface for split lock ring 60c.

Further, split lock ring 60c includes an outer identical to the combined height of cylindrical surface 104c and cylindrical wall 106c. Split lock ring 60c further includes an upper annular inclined surface 62c which extends inwardly and downwardly in a converging manner from the upper end of cylindrical surface 64c at an angle substantially identical to that of superior guide surface 102c. Further, split lock ring 60c includes a lower convex V-shaped annular surface 116c comprised of a frusto-conical annular lower surface 118c which extends downwardly and inwardly in a converging manner form the lower end of cylindrical surface 64c and a frusto-conical annular lower surface 120c which extends inwardly and upwardly from the inner edge of annular surface 118c in a converging manner. It will be appreciated that convex V-shaped annular surface 116c has a configuration substantially identical to that of concave V-shaped annular surface 110c of insert rim 32c. Further, the distance between upper frusto-conical surface 62c and frusto-conical annular lower surface 118c is substantially identical to the distance between superior guide surface 102c and frusto-conical annular surface 112c. As a result, split lock ring 60c fits within recess 100c with a very small free space in the vertical direction thereof. As a result, annular lower surface 118c can slide along annular surface 112c, while superior guide surface 102c guides upper frusto-conical surface 62c. Because of this arrangement, split lock ring 60c can be made larger than the corresponding ring of U.S. Pat. No. 4,241,463 to Khovaylo, and consequently, annular inner inclined arcuate surface 68c thereof can be made larger with greater overlap of femoral head 78c. This is because there is no need to provide the free space for vertical movement of the split lock ring as in the Khovaylo patent.

Thus, in operation, when femoral head 78c is inserted through the open end of insert rim 32c, that is, through the space defined by inner frusto-conical wall surface 54c, femoral head 78c thereof contacts annular beveled surface 70c of split lock ring 60c. Further advancement of femoral head 78c results in movement of split lock ring 60c outwardly in recess 100c until femoral head 78c passes therethrough. Thereafter, spring rod 74c causes compression of split lock ring 60c to the position shown in FIG. 3 in order to lock femoral head 78c in such position. It will be appreciated that unlike the embodiments of FIGS. 1A-1E and 2, upper frusto-conical surface 62c of split lock ring 60c is always in contact with superior guide surface 102c of bearing insert 24c, so that arcuate surface 68c of split lock ring 60c forms an actual continuation of inner substantially hemispherical bearing surface 28c of bearing insert 24c, whereby arcuate surface 68c provides larger femoral head overlap than the aforementioned embodiments of FIGS. 1A-1E and 2.

It will be appreciated that, in the locked position of FIG. 3, a downward pulling force on femoral head 78c will not result in disengagement of femoral head 78c from bearing insert 24c. This is because of annular surfaces 112c and 114c of insert rim 32c.

It will further be appreciated that, in the embodiment of FIG. 3, as well as all of the embodiments of the present invention, the rotational center 122c of femoral head 78c is purposely displaced in a polar direction from the rotational center 124c of acetabular snell 12c by approximately 2 mm. In this manner, the resulting eccentricity causes the hip joint reaction force to vector through rotational center 124c of acetabular shell 12c to produce an unbalanced torque, which motors or rotates acetabular shell 12c around the rotational center 122c thereof to achieve a more centered axial position or valgus orientation which is a more favorable orientation in situ. The ensuing rotational displacement or cone of motion is limited within a design range of approximately 30° about the center line through femoral head 78c and femoral neck 80c. The limit of rotational motion is reached when femoral neck 80c contacts the frusto-conical wall surface 54c of insert rim 32c.

Referring now to FIG. 4, an implantable prosthetic joint 10d according to another embodiment of the present invention will now be described, in which elements corresponding to those described above with respect to implantable prosthetic joint 10a are identified by the same reference numerals, with the exception that the letter "a" is replaced by the letter "d" following the respective numeral. A detailed description of the identical elements will be omitted herein for the sake of brevity.

Specifically, acetabular shell 12d, bearing insert 24d and the femoral head (not shown) are substantially identical to the corresponding elements of implantable prosthetic joint 10a of FIGS. 1A-1E, with the exception that the width of skirt portion 18d is increased and is formed with a horizontal ledge 126d on inner spherical surface 16d, extending partially therearound at the transition area between substantially hemispherical shell portion 13d and skirt portion 18d. In correspondence therewith, outer substantially hemispherical domed surface 26d of bearing insert 24d is formed with a shoulder 128d which seats on ledge 126d in order to retain bearing insert 24d in the position shown in FIG. 4. The reason for this, as will be explained in greater detail herein below, is that insert rim 32d is retractable as shown at the left side of FIG. 4, so that it is necessary to provide horizontal ledge 126d to retain bearing insert 24d in the upper position when insert rim 32d is moved to its lower position.

Insert rim 32d is similar in configuration to insert rim 32a, with the exception that steps 42a and 44a are eliminated. Instead, inner ring surface 31d thereof is formed by an annular inclined inner wall surface 46d which extends inwardly and downwardly in a converging manner from annular planar upper surface 38d, and which terminates at its lower end at an annular lower planar surface 66d that extends inwardly therefrom. In addition, insert rim 32d is formed with an outer annular flange 130d which covers the lower free end 108d of skirt portion 18d of acetabular shell 12d, as shown at the right side of FIG. 4, so as to provide a substantially continuous surface from outer spherical surface 20d to outer annular flange 130d.

It is important to note that, in the embodiment of FIG. 4, insert rim 32d is split, as at 132d. and ring 60d is likewise split, as at 133d. As a result, insert rim 32d and ring 60d can be compressed in order to move them from the lower unassembled position shown in the left side of FIG. 4 to the upper secured position shown at the right side of FIG. 4. As will be appreciated from the discussion which follows, this arrangement provides distinct advantages from that disclosed in U.S. Pat. Nos. 3,818,512; 3,889,299; 4,380,090; and 4,770,661, since insert rim 32d is merely biased upwardly to the position shown in the right side of FIG. 4 to lock the femoral head therein. Such biasing occurs by the surgeon merely pressing insert rim 32d upwardly with mild finger pressure. Thus, space problems encountered with the prior art structures do not occur with the present invention since there is no turning, screwing or the like motion involved.

With this arrangement, split lock ring 60d sits along inner ring surface 31d, and it is caused to move to the upper and lower positions of FIG. 4 with insert rim 32d. As a result, since no free vertical space is necessary to move split lock ring 60d, as in the embodiment of FIGS. 1A-1E and 2, annular inner arcuate surface 68d of split 35 lock ring 60d can be made of a larger dimension so as to increase the effective bearing contact surface with the femoral head.

Referring now to FIGS. 5 and 6, an implantable prosthetic joint 10e according to another embodiment of the present invention will now be described, in which elements corresponding to those described above with respect to implantable prosthetic joint 10d are identified by the same reference numerals, with the exception that the letter "d" is replaced by the letter "e" following the respective numeral. A detailed description of the identical elements will be omitted herein for the sake of brevity.

As shown therein, implantable prosthetic joint 10e differs from implantable prosthetic joint 10d in the manner in which insert rim 32e is engaged with skirt portion 18e of acetabular shell 12e. Specifically, in place of rib 34d and groove 36d, inner cylindrical surface 22e is formed with a plurality of circular, axially spaced, concentric threads or grooves 134e and, in like manner, outer cylindrical surface 40e of insert rim 32e is formed with a plurality of circular, axially spaced, concentric threads or grooves 136e which matingly engage with threads 134e. As with insert rim 32d, insert rim 32e is also split, as at 132e. In this manner, insert rim 32e can be compressed to disengage threads 134e and 136e from each other in order to lower insert rim 32e, and split lock ring 60e engaged thereby, to the position shown in FIG. 6. Then, the femoral head can be positioned within bearing insert 24e, whereupon insert rim 32e is once again biased upwardly to the position shown in FIG. 5. Thus, threads 134e and 136e provide an alternative to rib 34d and groove 36d of implantable prosthetic joint 10d and can be used in place thereof in any of the aforementioned embodiments.

It will be appreciated that inner ring surface 31e of insert rim 32e includes an upper step 42e and a lower step 44e, with split lock ring 30e including a corresponding configuration along the outer annular surface thereof.

In operation, as shown in FIG. 6, insert rim 32a is moved to the lower position shown therein in which the upper threads 136e of insert rim 32e only engage the lower threads 134e of acetabular shell 12e. Initially, in such position, split lock ring 60e rests on upper and lower steps 42e and 44e of insert rim 32e. Upon advancement of the femoral head through insert rim 32e, the femoral head thereof contacts beveled surface 70e of split lock ring 60e. Further advancement of the femoral head results in movement of split lock ring 60e vertically upward to the position shown in FIG. 6, until the upper planar surface 62e thereof abuts against outer face 30e of bearing insert 24e, without outward expansion of split lock ring 60e. Thereafter, further advancement of the femoral head results in the femoral head biasing split lock ring 60e apart, that is, in the outward direction, until outer annular wall 96e thereof abuts against inner cylindrical wall 86e of upper step 42e of inner ring surface 31e. In this position, the femoral head passes through split lock ring 60e, whereupon split lock ring 60e is biased to the contracted position shown in FIG. 6 by spring rod 74e. Thereafter, split lock ring 60e falls back to the position on upper and lower steps 42e and 44e of insert rim 32e. Then, insert rim 32e is merely pushed up by an external force, thereby also pushing up split lock ring 60e to a further extent, to the position shown in FIG. 5, whereupon all of threads 134e and 136e are in engagement with each other in order to lock the femoral head in place. During such pushing up, there will be a clicking sound as the threads engage and ride over each other.

It will be appreciated that, with the embodiments of FIGS. 5 and 6, insert rim 32e is always engaged with acetabular shell 12e so that no loose parts are present. Further, with this arrangement, inner arcuate surface 68e of split lock ring 60e can be made larger than that of the prior art since the space required to move split lock ring 60e upwardly in order to permit entry of the femoral head in bearing insert 24e varies in dependence upon the position of insert rim 32e.

The embodiment of FIG. 7 is substantially identical to that of FIGS. 5 and 6, with the exception that external threads 136e are replaced by two vertically or axially spaced circumferential ribs 138f and 140f, and threads 134e are replaced by two vertically spaced circumferential grooves 142f and 144f, respectively. Thus, with this embodiment, in the inirial set-up position, upper rib 138f is engaged within lower groove 144f as shown in FIG. 7. After the femoral head has been inserted into bearing insert 24f, in the manner discussed above with respect to the embodiments of FIG. 5 and 6, insert rim 32f is biased upwardly until upper rib 138f is engaged within upper groove 142f and lower rib 140f is engaged within lower groove 144f. This provides for double retention or redundant locking, and improved strength of the assembly.

It will be appreciated that rib 138f and groove 142f are of a lesser diameter than rib 140f and groove 144f, respectively. This is provided in order to permit easier insertion where there are two or more ribs.

Referring now to FIGS. 8A-8D. an implantable prosthetic joint 10g according to another embodiment of the present invention will now be described, in which elements corresponding to those described above with respect to implantable prosthetic joint 10a are identified by the same reference numerals, with the exception that the letter "a" is replaced by the letter "g" following the respective numeral. A detailed description of the identical elements will be omitted herein for the sake of brevity.

As shown in FIG. 8A, acetabular shell 12g, bearing insert 24g and femoral head 78g are substantially identical to the corresponding elements of implantable prosthetic joint 10a of FIGS. 1A-1E, with the exception that inner cylindrical surface 22g of skirt portion 18g includes a shoulder 146g so as to separate inner cylindrical surface 22g into an upper, inner cylindrical surface 148g and a lower inner cylindrical surface 150g, with lower cylindrical surface 150g having a greater diameter than upper cylindrical surface 148g.

Bearing insert 32g is formed in a similar manner to bearing insert 32a, with the following exceptions.

Inner wall surface 54g is formed in a frusto-conical configuration in much the same manner as inner wall surface 54c of implantable prosthetic joint 10c, that is, with a frusto-conical configuration that diverges inwardly and upwardly. Further, insert rim 32g includes a single step 42g. However, inner wall surfaces 46g and 50g are cylindrical surfaces, rather than being inclined, with the exception that the upper half of inner wall surface 46g is formed as a frusto-conical surface 152g which is inclined upwardly and inwardly in a diverging manner and terminates at planar upper surface 38g. Finally, it will be appreciated that the outer diameter of outer cylindrical surface 40g is substantially identical to the inner diameter of lower inner cylindrical surface 150g. As a result insert rim 32g is limited in its upward travel until planar upper surface 38g abuts against shoulder 146g of acetabular shell 12g, so as to provide an annular space 154g between upper surface 38g of insert rim 32g and outer face 30g of bearing insert 24g, the reason for which will be apparent from the description hereinafter.

Figure 8B:
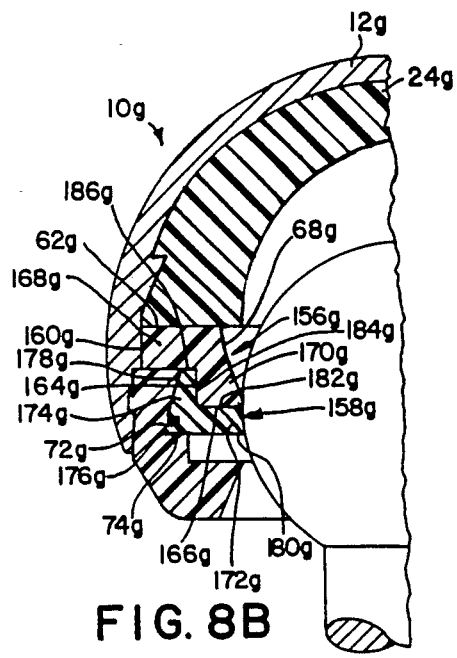
FIG. 8B is a cross-sectional view of the portion of the implantable prosthetic joint of FIG. 8A, showing the femoral head partially inserted therein.

In the embodiment of FIGS. 8A-8D, split lock ring 60 is formed by an upper lock ring section 156g and a lower lock ring section 158g. Upper lock ring section 156g includes an upper annular surface 62g and an inner annular arcuate surface 68g extending downwardly from the inner edge of upper annular surface 62g. It will be appreciated that upper lock ring section 156g, as shown in FIG. 8B, has a substantially L-shaped cross-sectional configuration and is therefore formed with an outer cylindrical surface 160g extending downwardly from upper annular surface 62g, a horizontal annular surface 162g extending inwardly from the lower edge of outer cylindrical surface 160g, an outer cylindrical surface 164g extending downwardly from the inner edge of horizontal annular surface 162g and a lower horizontal annular surface 166g extending between the lower edges of inner arcuate surface 68g and outer cylindrical surface 164g It will be appreciated from FIGS. 8A and 8B that upper lock ring section 156g thereby forms a horizontal leg 168g and a vertical leg 170g extending downwardly from the inner end of horizontal leg 168g. Further, it will be appreciated that the height of horizontal leg 168g is substantially identical to the height of annular space 154g such that upper lock ring section 156g moves between the horizontal positions shown in FIGS. 8A and 8B and is restrained from moving in the vertical direction of such figures.

Lower lock ring section 158g also has a substantially L-shaped cross-sectional configuration with an inner horizontal leg 172g and an outer, upwardly extending vertical leg 174g in cross-section. Specifically, lower lock ring section 158g includes an outer cylindrical surface 176g which leads into a frusto-conical surface 178g at the upper end thereof, with outer cylindrical surface 176g and frusto-conical surface 178g having dimensions and shape substantially identical to those of inner wall surface 46g and frusto-conical surface 152g of insert rim 32g so as to mate therewith as shown in FIG. 8B. Lower lock ring section 158g includes a lower annular planar surface 180g which extends inwardly from the lower edge of outer cylindrical surface 176g and terminates in a beveled surface 70g extending upwardly and inwardly in a converging manner. A horizontal annular surface 182g extends inwardly from the upper edge of beveled surface 70g, and an inner cylindrical surface 184g extends upwardly from the inner edge thereof. Finally, an upper annular horizontal surface 186g connects the upper ends of frusto-conical surface 178g and inner cylindrical surface 184g. It is noted that circumferential groove 72g is formed in outer cylindrical surface 176g, with spring rod 74g positioned therein. This is because this portion is thicker than the corresponding portion of frusto-conical surface 178g of vertical leg 174g.

Figure 8C:
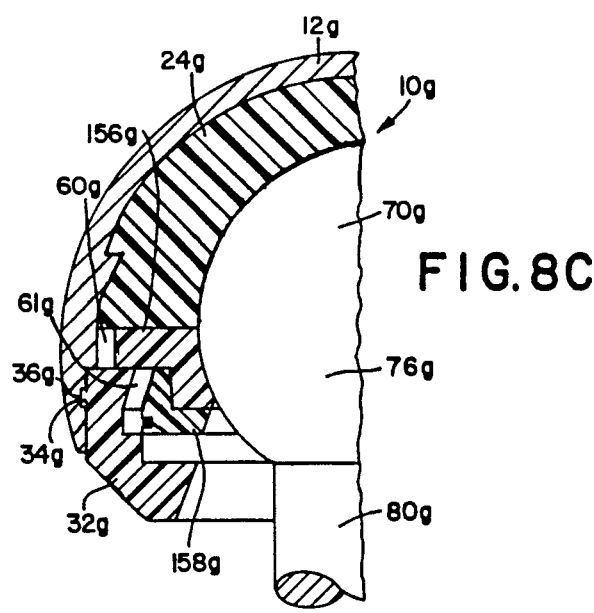
FIG. 8C is a cross-sectional view of the portion of the implantable prosthetic joint of FIG. 8A, showing the femoral head fully inserted within the bearing insert and with the retaining ring at its uppermost position.
Figure 8D:
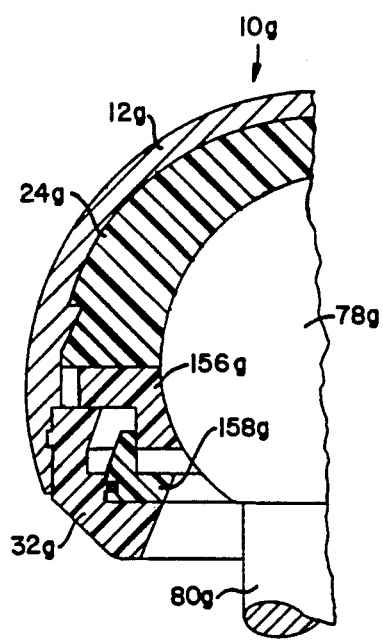
FIG. 8D is a cross-sectional view of the portion of the implantable prosthetic joint of FIG. 8A, showing the final assembly position thereof.

In the initial position, prior to insertion of femoral head 78g within bearing insert 24g, insert rim 32g is secured to acetabular shell 12g by means of rib 34g and groove 36g. In such initial position, upper lock ring section 156g assumes the position shown in FIG. 8A, while lower lock ring section 158g is positioned on inner ring surface 31g. In operation, femoral head 78g is inserted through the opening in insert rim 32g, that is, through the circular space defined by inner wall surface 54g of insert rim 32g until femoral head 78g thereof contacts beveled surface 70g of lower lock ring section 158g. Further advancement of femoral head 78g results in movement of lower lock ring section 158g vertically upward to the position shown in FIG. 8A until upper annular horizontal surface 186g abuts against horizontal annular surface 62g of upper lock ring section 156g and horizontal annular surface 182g of lower lock ring section 158g abuts against lower horizontal annular surface 166g of upper lock ring section 156g. In this regard, it will be appreciated that the height of outer cylindrical surface 164g of upper lock ring section 156g is substantially identical to the height of inner cylindrical surface 184g of lower lock ring section 158g. Further, because of spring rod 74g, outer cylindrical surface 164g is engaged against inner cylindrical surface 184g. Upon continued advancement of femoral head 78g, upper lock ring section 156g engaged thereby is biased outwardly to the position shown in FIG. 8B, thereby also carrying lower lock ring section 158b to such position against the force of spring rod 74g. Upon continued advancement of femoral head 78g into bearing insert 24g, as shown in FIG. 8C, spring rod 74g biases lower lock ring section 158g to its contracted position, thereby also biasing upper lock ring section 156g to its contracted position. Thereafter, lower lock ring section falls back down to its initial position on inner ring surface 31g of insert rim 32, as shown in FIG. 8D.

As with the aforementioned embodiments, it will be appreciated that inner annular arcuate surface 68g of split lock ring 60g can be made of a larger size than that of the prior art to provide a larger bearing surface for femoral head 78g of femoral head 78g, while also preventing accidental or inadvertent escape of femoral head 78g from bearing insert 24g, even in the presence of abnormal dislocation forces.

Figure 9:
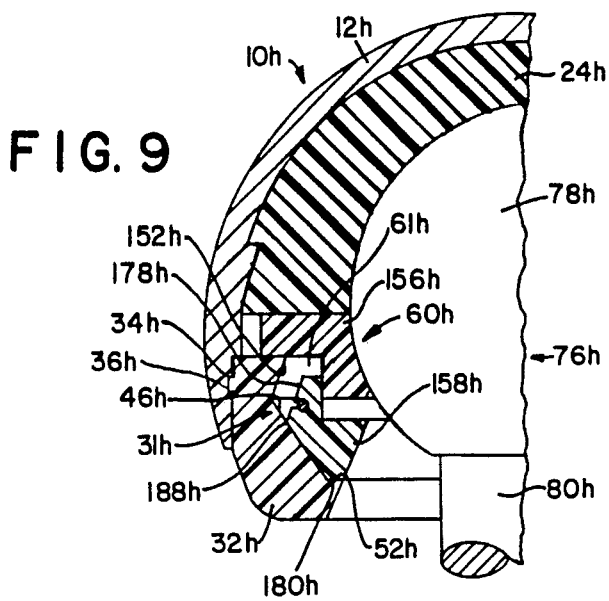
FIG. 9 is a cross-sectional view of a portion of an implantable prosthetic joint according to another embodiment of the present invention.

Referring now to FIG. 9, an implantable prosthetic joint 10h according to another embodiment of the present invention will now be described, in which elements corresponding to those described above with respect to implantable prosthetic joint 10g are identified by the same reference numerals, with the exception that the letter "g" is replaced by the letter "h" following the respective numeral. A detailed description of the identical elements will be omitted herein for the sake of brevity.

Specifically, acetabular shell 12h, bearing insert 24h, upper lock ring section 156h and femoral head 78h are identical to the corresponding elements of implantable prosthetic joint 10g of FIGS. 8A-8D.

The difference between implantable prosthetic joint 10h and implantable prosthetic joint 10g is that the inner ring surface 31h of insert rim 32h is formed with an inner frusto-conical surface 46h extending from the lower edge of inner frusto-conical surface 152h down to lower annular horizontal ledge 52h. In like manner, lower lock ring section 158h is formed with an outer frusto-conical surface 188g extending upwardly and outwardly in a diverging manner from lower annular planar surface 180h to frusto-conical surface 178h. Further, it is noted that rib 34h and groove 36h have a part-circular cross-sectional configuration.

In all other respects, implantable prosthetic joint 10h is identical to implantable prosthetic joint 10g and operates in a similar manner thereto.

Figure 10:
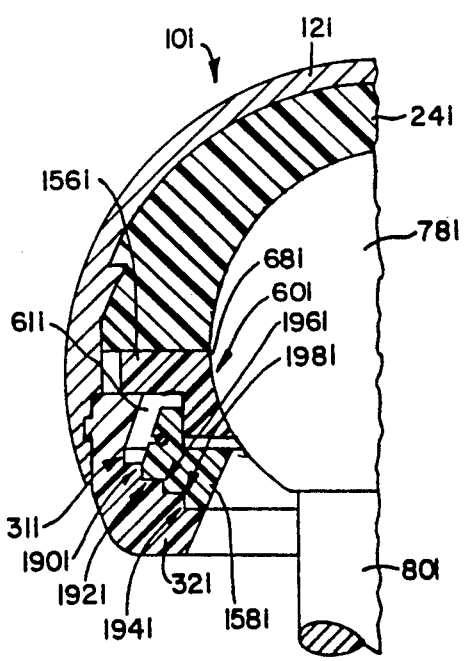
FIG. 10 is a cross-sectional view of a portion of an implantable prosthetic joint according to another embodiment of the present invention.

Referring now to FIG. 10, an implantable prosthetic joint 10i according to another embodiment of the present invention will now be described, in which elements corresponding to those described above with respect to implantable prosthetic joint 10g are identified by the same reference numerals, with the exception that the letter "g" is replaced by the letter "i" following the respective numeral. A detailed description of the identical elements will be omitted herein for the sake of brevity.

Implantable prosthetic joint 10i differs from implantable prosthetic joint 10g by providing a plurality of steps 190i, 192i and 194i at inner ring surface 31i of insert rim 32i in place of the single step 42g of insert rim 32g. In like manner, lower lock ring section 158i is formed with corresponding steps 196i and 198i which sit upon steps 190i and 192i, respectively, or steps 192i and 194i, respectively. The difference between implantable prosthetic joints 10i and 10g is similar to the difference between implantable prosthetic joints 10b and 10a. Because of the additional steps, the need for free space to move lower lock ring section 158i is reduced, so that arcuate surface 68i can be made larger. The remaining elements of implantable prosthetic joint 10i are substantially identical to those of implantable prosthetic joint 10g, and the operation thereof is also the same.

Figure 11:
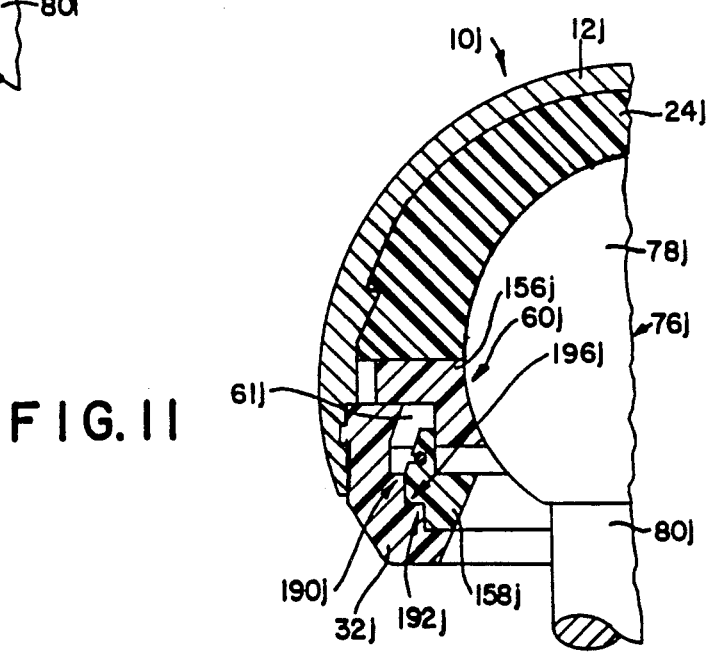
FIG. 11 is a cross-sectional view of a portion of an implantable prosthetic joint according to another embodiment of the present invention.

Implantable prosthetic joint 10j of FIG. 11 is also substantially identical to implantable prosthetic joints 10g and 10i, with the exception that insert rim 32j is provided with only two steps 190j and 192j, while lower lock ring section 158j is provided with a single step 196j.

Referring now to FIG. 12, an implantable prosthetic joint 10k according to another embodiment of the present invention will now be described, in which elements corresponding to those described above with respect to implantable prosthetic joint 10b are identified by the same reference numerals, with the exception that the letter "b" is replaced by the letter "k" following the respective numeral. A detailed description of the identical elements will be omitted herein for the sake of brevity.

With implantable prosthetic joint 10k, insert rim 32k is formed from an upper insert rim section 200k and a lower insert rim section 202k connected with upper rim section 200k. Specifically, inner cylindrical surface 22k of skirt portion 18k is formed with a plurality of barbs 204k or the like. Upper insert rim section 200k is formed by a main stepped portion 206k having an inner ring surface 31k formed with a plurality of steps 190k, 192k and 194k, a lower annular key section 208k and an upper annular extension 210k. Barbs 204k will cut into upper annular extension 210k of insert rim 32k, whereby plastic flow will occur so that insert rim 32k is restrained in acetabular shell 12a.

Lower insert rim section 202k includes a keyway 214k in the upper surface thereof for receiving key section 208k so as to lock lower insert rim section 202k to upper insert rim section 200k.

Split lock ring 60k is formed with a plurality of corresponding steps 216k and 218k for matingly seating on steps 190k, 192k and 194k.

In this regard, it will be appreciated that implantable prosthetic joint 10k operates in a substantially identical manner to implantable prosthetic joint 10b of FIG. 2. However, the number of steps is increased with respect to implantable prosthetic joint 10b, and steps 190k, 192k and 194k are formed as right angle steps, rather than inclined steps as in implantable prosthetic joint 10b.

Referring now to FIG. 13, an implantable prosthetic joint 10l according to another embodiment of the present invention will now be described, in which elements corresponding to those described above with respect to implantable prosthetic joint 10k are identified by the same reference numerals, with the exception that the letter "k" is replaced by the letter "l" following the respective numeral. A detailed description of the identical elements will be omitted herein for the sake of brevity.

Implantable prosthetic joint 10l differs from implantable prosthetic joint 10k in that insert rim 32l is formed as a single piece with only a single step 190l. The outer cylindrical surface 40l of insert rim 32l is deformed over barbs 204l at inner surface 22l of annular skirt portion 18l so as to retain insert rim 32l in the position shown in FIG. 13.

Split spring ring 60l is constructed in a similar manner to split spring ring 60a, with the exception that outer surface 64l thereof is of a cylindrical configuration, rather than a frusto-conical or inclined configuration. In all other respects, implantable prosthetic joint 10l operates in a similar manner to implantable prosthetic joint 10a.

Figure 15:
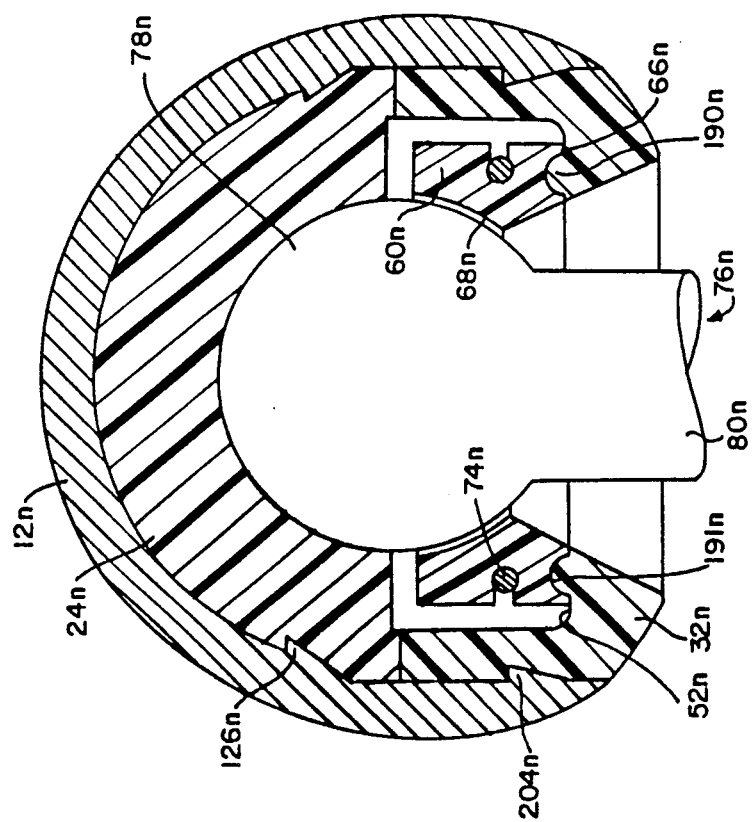
FIG. 15 is a cross-sectional view of a portion of an implantable prosthetic joint according to another embodiment of the present invention.

Implantable prosthetic joint 10m of FIG. 14 is substantially identical to implantable prosthetic joint 10k of FIG. 12, with the exception that insert rim 32m is constructed of a single piece and includes a circumferential groove 222m in outer cylindrical surface 40m thereof which receives an annular head 224m in inner cylindrical surface 22m of skirt portion 18m. In all other respects, implantable prosthetic joint 10m is identical to and operates in an identical manner to implantable prosthetic joint 10k of FIG. 12. Referring now to FIG. 15, an implantable prosthetic joint 10n according to another embodiment of the present invention will now be described, in which elements corresponding to those described above with respect to implantable prosthetic joint 10l of FIG. 13 are identified by the same reference numerals, with the exception that the letter "l" is replaced by the letter "n" following the respective numeral. A detailed description of the identical elements will be omitted herein for the sake of brevity.

In FIG. 15, step 190l is replaced by an annular bead 190n at the inner periphery of horizontal inwardly extending ledge 52n and has a semi-circular cross-sectional configuration. Further, split lock ring 60n includes an annular semi-circular groove 191n at the annular lower planar surface 66n thereof for receiving annular bead 190n. Accordingly, when inserting the femoral head, it is only necessary that split lock ring 60n ride up and over annular bead 190n. Since split lock ring 60n includes groove 191n which receives annular bead 190n, the amount of vertical space in FIG. 15 required for movement of split lock ring 60n during insertion of the femoral head is minimal so that inner annular inclined surface 68n thereof can be made large so as to increase the effective contact with femoral head 78n upon assembly.

Figure 16:
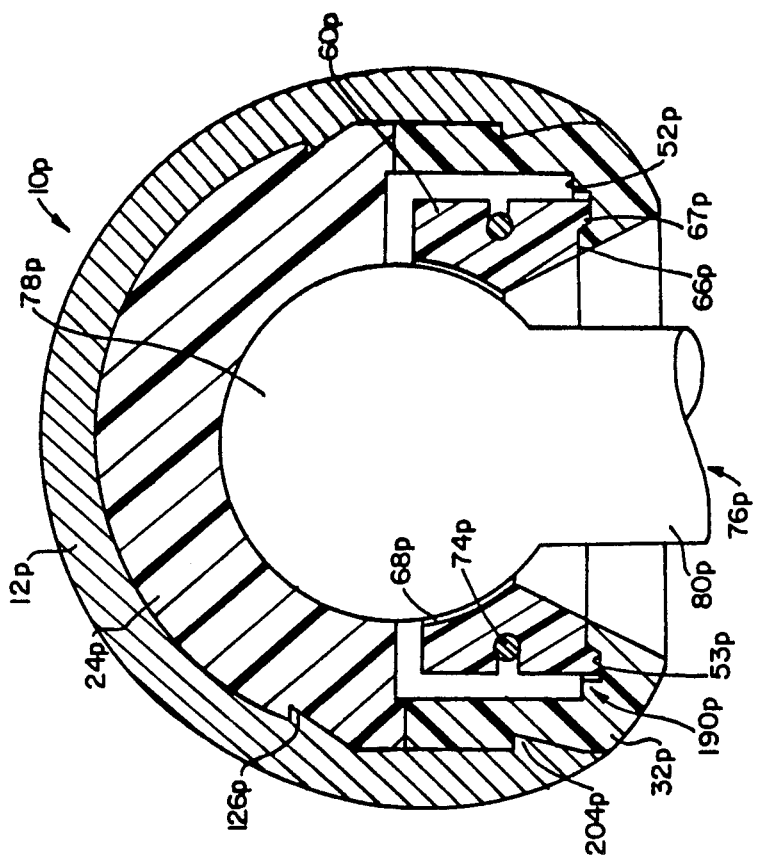
FIG. 16 is a cross-sectional view of a portion of an implantable prosthetic joint according to another embodiment of the present invention.

Referring now to FIG. 16, an implantable prosthetic joint 10p according to another embodiment of the present invention will now be described, in which elements corresponding to those described above with respect to implantable prosthetic joint 10n are identified by the same reference numerals, with the exception that the letter "n" is replaced by the letter "p" following the respective numeral. A detailed description of the identical elements will be omitted herein for the sake of brevity.

Implantable prosthetic joint 10p differs from implantable prosthetic joint 10n in that horizontal ledge 52p includes an annular groove 53p and annular lower planar surface 66p of split lock ring 60p includes an annular extension 67p which fits within groove 53p. In effect, the arrangement of groove 53p and extension 67p is the direct opposite of bead 190n and groove 191n, that is, the parts are reversed in the different elements. In this manner, a step 190p is formed in insert rim 32p.

It will therefore be appreciated that, with the present invention, an implantable prosthetic hip joint is provided in which insertion of the femoral head and the bearing insert is accomplished by a mere push of the femoral head therein. Further, the split lock ring can be constructed with greater dimensions than those of the prior art so as to provide an increased surface area of contact between the inner annular surface of the split lock ring and the femoral head, thereby improving the level of security relative to the torque required to produce premature escape of the femoral head. Further, with the present invention, use of different bearing materials is facilitated. Also, it is relatively easy for a surgeon to remove the femoral head from the bearing insert when necessary.

Having described specific preferred embodiments of the invention with reference to the accompanying drawings, it will be appreciated that the present invention is not limited to those precise embodiments, and that various changes and modifications can be effected therein without departing from the spirit or scope of the invention as defined by the appended claims.

What is claimed is:

1. An implantable prosthetic joint comprising:
   a) first bone securing means for constraining the prosthetic joint within a first bone of a biological joint, said first bone securing means including a spherical shell articulating within a socket in the first bone, said shell including an inner spherical surface and an open circumferential end;
   b) second bone securing means for securing the prosthetic joint to a second bone of the biological joint, said second bone securing means including a femoral head and stem means connected with said femoral head for securing the prosthetic joint to the second bone;
   c) bearing means for connecting said second bone securing means with said first bone securing means, said bearing means including:
      i) an outer spherical dome which engages with the inner spherical surface of said shell,
      ii) an open circumferential end,
      iii) an inner spherical surface which receives said femoral head for ball-and-socket movement therein, and
      iv) an inner annular surface at said open circumferential end, said inner annular surface including at least one annular step;
   d) split spring ring means for retaining said femoral head in said bearing means, said split spring ring means including an annular inner engaging surface biased into engagement with the femoral head when the femoral head is seated in said bearing means, and said split spring ring means engaged with said at least one annular step of said inner annular surface when said femoral head is fit within said bearing means; and
   e) said bearing means including a bearing insert having said outer spherical dome and said inner spherical surface, and an insert rim formed separate from and independent of said bearing insert, said insert rim being secured to said first bone securing means and having said open circumferential end, said inner annular surface, with an annular recess defined between said bearing insert and said insert rim for receiving said split spring ring means.

2. An implantable prosthetic joint according to claim 1; wherein said insert rim further includes connecting means for connecting said insert rim to said first bone securing means.

3. An implantable prosthetic joint according to claim 2; wherein said shell has a substantially hemispherical shell portion and a skirt portion continuous therewith and which defines said open circumferential end thereof, said substantially hemispherical shell portion including said inner spherical surface and said skirt portion including an inner substantially cylindrical surface continuous with said inner spherical surface.

4. An implantable prosthetic joint according to claim 3; wherein said first bone securing means includes one of groove means and mating rim means on said inner substantially cylindrical surface of said skirt portion, and the connecting means includes the other of said groove means and said rim means.

5. An implantable prosthetic joint according to claim 4; wherein said groove means includes first and second grooves spaced from each other and said rim means includes first and second rims for matingly engaging with the first and second grooves, respectively.

6. An implantable prosthetic joint comprising:
   a) first bone securing means for constraining the prosthetic joint within a first bone of a biological joint, said first bone securing means including a spherical shell articulating within a socket in the first bone, said shell including an inner spherical surface and an open circumferential end, said shell having a substantially hemispherical shell portion and a skirt portion continuous therewith and which defines said open circumferential end thereof, said substantially hemispherical shell portion including said inner spherical surface and said skirt portion including an inner substantially cylindrical surface continuous with said inner spherical surface, said first bone securing means further including a plurality of concentric, axially spaced threads on said substantially cylindrical inner surface of said skirt portion;
   b) second bond securing means for securing the prosthetic joint to a second bone of the biological joint, said second bone securing means including a femoral head and stem means connected with said femoral head for securing the prosthetic joint to the second bone;
   c) bearing means for connecting said second bone securing means with said first bone securing means, said bearing means including:
      i) an outer spherical dome which engages with the inner spherical surface of said shell,
      ii) an open circumferential end,
      iii) an inner spherical surface which receives said femoral head for ball-and-socket movement therein, and iv) an inner annular surface at said open circumferential end, said inner annular surface including at least one annular step;

d) split spring ring means for retaining said femoral head in said bearing means, said split spring ring means including an annular inner engaging surface biased into engagement with the femoral head when the femoral head is seated in said bearing means, and said split spring ring means engaged with said at least one annular step of said inner annular surface when said femoral head is fit within said bearing means; and e) said bearing means including a bearing insert having said outer spherical dome and said inner spherical surface, and an insert rim secured to said first bone securing means and having said open circumferential end, said inner annular surface, and connecting means for connecting said insert rim to said first bone securing means, with an annular recess defined between said bearing insert and said insert rim for receiving said split spring ring means, and said connecting means including a plurality of concentric, axially spaced threads on the outer surface of said insert rim for releasably engaging with said threads on said inner substantially cylindrical surface of said skirt portion.

7. An implantable prosthetic joint comprising:
a) first bone securing means for constraining the prosthetic joint within a first bone of a biological joint, said first bone securing means including a spherical shell articulating within a socket in the first bone, said shell including an inner spherical surface and an open circumferential end, said shell having a substantially hemispherical shell portion and a skirt portion continuous therewith and which defines said open circumferential end thereof, said substantially hemispherical shell portion including said inner spherical surface and said skirt portion including an inner substantially cylindrical surface continuous with said inner spherical surface, and said first bone securing means includes one of groove means and mating rim means on said inner substantially cylindrical surface of said skirt portion;

b) second bone securing means for securing the prosthetic joint to a second bone of the biological joint, said second bone securing means including a femoral head and stem means connected with said femoral head for securing the prosthetic joint to the second bone;

c) bearing means for connecting said second bone securing means with said first bone securing means, said bearing means including:
i) an outer spherical dome which engages with the inner spherical surface of said shell,
ii) an open circumferential end,
iii) an inner spherical surface which receives said femoral head for ball-and-socket movement therein, and
iv) an inner annular surface at said open circumferential end, said inner annular surface including at least one annular step;

d) split spring ring means for retaining said femoral head in said bearing means, said split spring ring means including an annular inner engaging surface biased into engagement with the femoral head when the femoral head is seated in said bearing means, and said split spring ring means engaged with said at least one annular step of said inner annular surface when said femoral head is fit within said bearing means; and e) said bearing means including a bearing insert having said outer spherical dome and said inner spherical surface, and an insert rim secured to said first bone securing means and having said open circumferential end, said inner annular surface, and connecting means for connecting said insert rim to said first bone securing means, the connecting means including the other of said groove means and said rim means, and said rim means includes a bead, with an annular recess defined between said bearing insert and said insert rim for receiving said split spring ring means.

8. An implantable prosthetic joint according to claim 3; wherein said first bone securing means includes barb means on said inner substantially cylindrical surface of said skirt portion for receiving said insert rim so as to connect said insert rim to said acetabular shell.

9. An implantable prosthetic joint according to claim 3; wherein said first bone securing means includes barb means on said inner spherical surface of said substantially hemispherical shell portion for receiving said outer spherical dome to secure said bearing insert to said acetabular shell.

10. An implantable prosthetic joint according to claim 1; wherein said inner annular surface includes an upper frusto-conical wall surface which extends downwardly and inwardly in a converging manner and has a lower edge and a lower annular ledge having an outer edge, said lower annular ledge engaging said split spring ring means to prevent pull-out of said femoral head from said bearing means, and said at least one annular step is formed between the lower edge of said upper frusto-conical wall surface and the outer edge of said lower annular ledge.

11. An implantable prosthetic joint comprising:
a) first bone securing means for constraining the prosthetic joint within a first bone of a biological joint, said first bone securing means including a spherical shell articulating within a socket in the first bone, said shell including an inner spherical surface and an open circumferential end;

b) second bone securing means for securing the prosthetic joint to a second bone of the biological joint, said second bone securing means including a femoral head and stem means connected with said femoral head for securing the prosthetic joint to the second bone;

c) bearing means for connecting said second bone securing means with said first bone securing means, said bearing means including:
i) an outer spherical dome which engages with the inner spherical surface of said shell,
ii) an open circumferential end,
iii) an inner spherical surface which receives said femoral head for ball-and-socket movement therein, aid
iv) an inner annular surface at said open circumferential end, said inner annular surface including at least one annular step;

d) split spring ring means for retaining said femoral head in said bearing means, said split spring ring means including an annular inner engaging surface biased into engagement with the femoral head when the femoral head is seated in said bearing means, and said split spring ring means engaged with said at least one annular step of said inner annular surface when said femoral head is fit within said bearing means;

e) said bearing means including a bearing insert having said outer spherical dome and said inner spherical surface, and an insert rim secured to said first bone securing means and having said open circumferential end and said inner annular surface, with an annular recess defined between said bearing insert and said insert rim for receiving said split spring ring means;

f) said inner annular surface includes an upper frusto-conical wall surface which extends downwardly and inwardly in a converging manner and has a lower edge and a lower annular ledge having an outer edge, said lower annular ledge engaging said split spring ring means to prevent pull-out of said femoral head from said bearing means, and said at least one annular step is formed between the lower edge of said upper frusto-conical wall surface and the outer edge of said lower annular ledge; and g) said inner annular surface includes one annular step formed by a frusto-conical surface extending upwardly and outwardly in a diverging manner from the outer edge of said lower annular ledge and having an upper edge, and an upper annular ledge connecting the lower edge of said upper frusto-conical wall surface and the upper edge of said lower frusto-conical wall surface, with a first diameter being defined by said upper frusto-conical wall surface and a second smaller diameter being defined by said lower frusto-conical wall surface.

12. An implantable prosthetic joint comprising:
a) a first bone securing means for constraining the prosthetic joint within a first bone of a biological joint, said first bone securing means including a spherical shell articulating within a socket in the first bone, said shell including an inner spherical surface and an open circumferential end;
b) second bond securing means for securing the prosthetic joint to a second bone of the biological joint, said second bone securing means including a femoral head and stem means connected with said femoral head for securing the prosthetic joint to the second bone;
c) bearing means for connecting said second bone securing means with said first bone securing means, said bearing means including:
   i) an outer spherical dome which engages with the inner spherical surface of said shell,
   ii) an open circumferential end,
   iii) an inner spherical surface which receives said femoral head for ball-and-socket movement therein, and
   iv) an inner annular surface at said open circumferential end, said inner annular surface including at least one annular step;
d) split spring ring means for retaining said femoral head in said bearing means, said split spring ring means including an annular inner engaging surface biased into engagement with the femoral head when the femoral head is seated in said bearing means, and said split spring ring means engaged with said at least one annular step of said inner annular surface when said femoral head is fit within said bearing means;
e) said bearing means including a bearing insert having said outer spherical dome and said inner spherical surface, and an insert rim secured to said first bone securing means and having said open circumferential end and said inner annular surface, with an annular recess defined between said bearing insert and said insert rim for receiving said split spring ring means;

f) said inner annular surface includes an upper frusto-conical wall surface which extends downwardly and inwardly in a converging manner and has a lower edge and a lower annular ledge having an outer edge, said lower annular ledge engaging said split spring ring means to prevent pull-out of said femoral head from said bearing means, and said at least one annular step is formed between the lower edge of said upper frusto-conical wall surface and the outer edge of said lower annular ledge; and g) said inner annular surface includes two successively connected annular steps connected between the outer edge of said lower annular ledge and said lower edge of said upper frusto-conical wall surface, each said step including a frusto-conical wall surface and an annular ledge.

13. An implantable prosthetic joint comprising:
a) first bone securing means for constraining the prosthetic joint within a first bone of a biological joint, said first bone securing means including a spherical shell articulating within a socket in the first bone, said shell including an inner spherical surface and an open circumferential end;
b) second bone securing means for securing the prosthetic joint to a second bone of the biological joint, said second bone securing means including a femoral head and stem means connected with said femoral head for securing the prosthetic joint to the second bone;
c) bearing means for connecting said second bone securing means with said first bone securing means, said bearing means including:
   i) an outer spherical dome which engages with the inner spherical surface of said shell,
   ii) an open circumferential end,
   iii) an inner spherical surface which receives said femoral head for ball-and-socket movement therein, and
   iv) an inner annular surface at said open circumferential end, said inner annular surface including at least one annular step;
d) split spring ring means for retaining said femoral head in said bearing means, said split spring ring means including an annular inner engaging surface having a lower portion spaced from the femoral head when the femoral head is seated in said bearing means, and said split spring ring means engaged with said at least one annular step of said inner annular surface when said femoral head is fit within said bearing means, said annular inner engaging surface being inclined in a converging manner toward said open circumferential end;
e) said bearing means including a bearing insert having said outer spherical dome and said inner spherical surface, and an insert rim secured to said first bone securing means and having said open circumferential end and said inner annular surface, with an annular recess defined between said bearing insert and said insert rim for receiving said split spring ring means; and
f) said inner annular surface includes an upper substantially cylindrical wall surface which has a lower edge and a lower annular ledge having an outer edge, said lower annular ledge engaging said split spring ring means to prevent pull-out of said femoral head from said bearing means, and said at least one annular step is formed between the lower edge of said upper substantially cylindrical wall surface and the outer edge of said lower annular ledge.

14. An implantable prosthetic joint according to claim 13; wherein said inner annular surface includes two successively connected annular steps connected between the outer edge of said lower annular ledge and said lower edge of said upper substantially cylindrical wall surface, each said step including a substantially cylindrical wall surface and an annular ledge.

15. An implantable prosthetic joint according to claim 1; wherein said split spring ring means includes a split lock ring and spring means for biasing said split lock ring into a compressed condition.

16. An implantable prosthetic joint comprising:
a) first bone securing means for constraining the prosthetic joint within a first bone of a biological joint, said first bone securing means including a spherical shell articulating within a socket in the first bone, said shell including an inner spherical surface and an open circumferential end, and said shell further including a substantially hemispherical shell portion and a skirt portion continuous therewith and which defines said open circumferential end, said substantially hemispherical shell portion including said inner spherical surface and said skirt portion including an inner substantially cylindrical surface continuous with said inner spherical surface;
b) second bone securing means for securing the prosthetic joint to a second bone of the biological joint, said second bone securing means including a femoral head and stem means connected with said femoral head for securing the prosthetic joint to the second bone;
c) bearing means for connecting said second bone securing means with said first bone securing means, said bearing means including:
i) an outer spherical dome which engages with the inner spherical surface of said shell,
ii) an open circumferential end,
iii) an inner spherical surface which receives said femoral head for ball-and-socket movement therein, and
iv) an inner annular surface at said open circumferential end, said inner annular surface including at least one annular step;
d) split spring ring means for retaining said femoral head in said bearing means, said split spring ring means including an annular inner engaging surface having a lower portion spaced from the femoral head when the femoral head is seated in said bearing means, and said split spring ring means engaged with said at least one annular step of said inner annular surface when said femoral head is fit within said bearing means, said annular inner engaging surface being inclined in a converging manner toward said open circumferential end; and
e) said bearing means including a bearing insert having said outer spherical dome and said inner spherical surface, and an insert rim secured to said first bone securing means and having said open circumferential end and said inner annular surface, with an annular recess defined between said bearing insert and said insert rim for receiving said split spring ring means, and said insert rim further including an outer exposed inclined annular surface extending inwardly and downwardly in a converging manner from the outer edge of said skirt portion.

17. An implantable prosthetic joint comprising:
a) first bone securing means for constraining the prosthetic joint within a first bone of a biological joint, said first bone securing means including a spherical shell articulating within a socket in the first bone, said shell including an inner spherical surface and an open circumferential end;
b) second bone securing means for securing the prosthetic joint to a second bone of the biological joint, said second bone securing means including a femoral head and stem means connected with said femoral head for securing the prosthetic joint to the second bone;
c) bearing means for connecting said second bone securing means with said first bone securing means, said bearing means including:
i) an outer spherical dome which engages with the inner spherical surface of said shell,
ii) an open circumferential end,
iii) an inner spherical surface which receives said femoral head for ball-and-socket movement therein, and
iv) an inner annular surface at said open circumferential end, said inner annular surface including at least one annular step having a substantially semi-circular groove for receiving said step.
d) split spring ring means for retaining said femoral head in said bearing means, said split spring ring means including an annular inner engaging surface spaced at least partially from the femoral head when the femoral head is seated in said bearing means, said annular inner engaging surface being inclined in a converging manner toward said open circumferential end, said split spring ring means engaged with said at least one annular step of said inner annular surface when said femoral head is fit within said bearing means, and said slit ring means including a bottom annular surface having an annular semi-circular groove for receiving said step.

18. An implantable prosthetic joint comprising:
a) first bone securing means for constraining the prosthetic joint within a first bone of a biological joint, said first bone securing means including a spherical shell articulating within a socket in the first bone, said shell including an inner spherical surface and an open circumferential end;
b) second bone securing means for securing the prosthetic joint to a second bone of the biological joint, said second bone securing means including a femoral head and stem means connected with said femoral head for securing the prosthetic joint to the second bone;
c) bearing means for connecting said second bone securing means with said first bone securing means, said bearing means including:
i) an outer spherical dome which engages with the inner spherical surface of said shell,
ii) an open circumferential end,
iii) an inner spherical surface which receives said femoral head for ball-and-socket movement therein, iv) an inner annular surface at said open circumferential end, said inner annular surface including at least one annular step, and v) said inner annular surface of said bearing means includes an annular groove adjacent said at least one annular step; and d) split spring ring means for retaining said femoral head in said bearing means, said split spring ring means including an annular inner engaging surface biased into engagement with the femoral head when the femoral head is seated in said bearing means, and said split spring ring means engaged with said at least one annular step of said inner annular surface when said femoral head is fit within said bearing means, and said split ring means includes an annular extension which fits in said annular groove.

19. An implantable prosthetic joint comprising:

a) first bone securing means for constraining the prosthetic joint within a first bone of a biological joint, said first bone securing means including a spherical shell articulating within a socket in the first bone, said shell including an inner spherical surface and an open circumferential end;

b) second bone securing means for securing the prosthetic joint to a second bone of the biological joint, said second bone securing means including a femoral head and stem means connected with said femoral head for securing the prosthetic joint to the second bone;

c) bearing means for connecting said second bone securing means with said first bone securing means, said bearing means including:

i) an open circumferential end, ii) an outer spherical dome which engages with the inner spherical surface of said shell, iii) an inner spherical surface which receives said femoral head for ball-and-socket movement therein, and iv) an annular recess in said inner spherical surface, said annular recess being defined by an upper annular inclined wall and a lower annular inclined wall, said upper and lower annular inclined walls being inclined upwardly away from said open circumferential end; and d) split spring ring means for retaining said femoral head in said bearing means, said split spring ring means including an annular inner engaging surface biased into engagement with the femoral head when the femoral head is seated in said bearing means, and said split spring ring means being slidably positioned in said annular recess and including an annular upper inclined surface and a lower annular inclined surface, said upper and lower annular inclined surfaces being inclined upwardly away from said open circumferential end, and the distance between said upper and lower annular surfaces being only slightly smaller than the distance between said upper and lower annular walls.

20. An implantable prosthetic joint according to claim 19; wherein said bearing means includes a bearing insert having said outer spherical dome, said inner spherical surface and said upper inclined wall, and an insert rim having said lower annular inclined wall and said open circumferential end, with said annular recess being defined between said bearing insert and said insert rim.

21. An implantable prosthetic joint according to claim 20; wherein said shell includes a substantially hemispherical shell portion defining said inner spherical surface and a skirt portion extending from said substantially hemispherical shell portion and defining said open circumferential end.

22. An implantable prosthetic joint according to claim 21; wherein said skirt portion includes an inner substantially cylindrical surface having first connecting means and said insert rim includes an outer substantially cylindrical surface for engaging with said inner substantially cylindrical surface of said skirt portion, said outer substantially cylindrical surface including second connecting means for matingly engaging with said first connecting means to connect said insert rim to said skirt portion.

23. An implantable prosthetic joint according to claim 22; wherein said first connecting means includes one of groove means and mating rim means on said inner substantially cylindrical surface of said skirt portion, and the first connecting means includes the other of said groove means and said rim means.

24. An implantable prosthetic joint according to claim 19; wherein said lower annular inclined wall includes an inner edge and said bearing means further includes a second lower annular inclined wall extending upwardly and inwardly in a converging manner from the inner edge of said first-mentioned lower annular inclined wall so as to define a substantially concave V-shaped lower annular wall therewith; and said split spring means includes a convex substantially V-shaped lower annular surface for matingly engaging with said V-shaped recess, said V-shaped lower annular inclined surface including said first-mentioned lower annular inclined surface of said split spring ring means, such that said first-mentioned lower annular inclined wall forms a guide ramp for movement of said split spring ring means thereon and said second lower annular inclined wall prevents escape of said split spring ring means from said annular recess.

25. An implantable prosthetic joint according to claim 20; wherein said bearing insert includes an outer annular face and said upper inclined wall is formed in said outer annular face.

26. An implantable prosthetic joint comprising:

a) first bone securing means for constraining the prosthetic joint within a first bone of a biological joint, said first bone securing means including a spherical shell articulating within a socket in the first bone, said shell including an inner spherical surface and an open circumferential end;

b) second bone securing means for securing the prosthetic joint to a second bone of the biological joint, said second bone securing means including a femoral head and stem means connected with said femoral head for securing the prosthetic joint to the second bone;

c) bearing means for connecting said second bone securing means with said first bone securing means, said bearing means including:

i) a bearing insert having an outer spherical dome which engages with the inner spherical surface of said shell and an inner spherical surface which receives said femoral head for ball-and-socket movement therein, and ii) a retractable annular split rim positioned below said bearing insert and including a central opening which permits passage of said femoral head therethrough and an inner ring surface, said retractable split rim including securing means for releasably securing said split rim in a first position spaced from said bearing insert and a second position at least substantially in contact with said bearing insert, an annular recess being defined between said bearing insert and said split rim when said split rim is secured in said first position; and d) split spring ring means for retaining said femoral head in said bearing means, said split spring ring means including an annular inner engaging surface biased into engagement with said femoral head and being positioned between said bearing insert and said retractable split rim, said split spring ring means being movable in said annular recess when said split rim is secured in said first position and being held by said inner ring surface when said split rim is secured in said second position.

27. An implantable prosthetic joint according to claim 26; wherein said inner ring surface includes at least one inner annular stepped portion for seating said split spring ring means when said split rim is secured in said second position.

28. An implantable prosthetic joint according to claim 26; wherein said inner ring surface includes an inner frusto-conical surface which extends inwardly and downwardly in a converging manner.

29. An implantable prosthetic joint according to claim 26; wherein said shell includes a substantially hemispherical shell portion defining said inner spherical surface and a depending skirt portion extending from said substantially hemispherical shell portion and defining said open circumferential end, said skirt portion including an inner substantially cylindrical surface, said inner substantially cylindrical surface including engaging means and said retractable split rim including an outer substantially cylindrical surface including said securing means for mating with said engaging means to releasably secure said split rim in said first and second positions.

30. An implantable prosthetic joint according to claim 29; wherein said engaging means includes a plurality of axially spaced circumferential threads on the inner substantially cylindrical surface of said skirt portion and said securing means includes a plurality of axially spaced circumferential threads on the outer substantially cylindrical surface of said retractable split rim which matingly engage with the axially spaced circumferential threads of said engaging means to releasably secure the retractable split rim in said first and second positions.

31. An implantable prosthetic joint according to claim 29; wherein said engaging means includes one of groove means and mating rim means on the inner substantially cylindrical surface of said skirt portion; and said securing means includes the other of said groove means and rim means on the outer substantially cylindrical surface of said retractable split rim.

32. An implantable prosthetic joint according to claim 31; wherein said groove means includes first and second spaced grooves and said rim means includes first and second spaced rims for engaging with said first and second grooves, respectively, in said second position and in which said first rim engages only with said second groove in said first position.

33. An implantable prosthetic joint according to claim 26; wherein said split spring ring means includes a split lock ring and spring means for biasing said split lock ring into a compressed condition.

34. An implantable prosthetic joint comprising:

a) first bone securing means for constraining the prosthetic joint within a first bone of a biological joint, said first bone securing means including a spherical shell articulating within a socket in the first bone, said shell including an inner spherical surface and an open circumferential end;

b) second bone securing means for securing the prosthetic joint to a second bone of the biological joint, said second bone securing means including a femoral head and stem means connected with said femoral head for securing the prosthetic joint to the second bone;

c) bearing means for connecting said second bone securing means with said first bone securing means, said bearing means including:
   i) a bearing insert having an outer spherical dome which engages with the inner spherical surface of said shell and an inner spherical surface which receives said femoral head for ball-and-socket movement therein, and
   ii) an insert rim positioned below said bearing insert, said insert rim including:
   A) an open circumferential end,
   B) an upper surface spaced from said bearing insert to define a guideway, and
   C) an inner annular ring surface, an annular recess being defined between said bearing insert and said inner ring surface of said insert rim, said inner ring surface including a lower ledge; and d) split spring ring means for retaining said femoral head in said bearing means, said split spring ring means including:
   i) an upper split lock ring section having a sliding section slidable within said guideway and an inner engaging surface biased into engagement with the femoral head when the femoral head is seated in said bearing means, and
   ii) a lower split lock ring section positioned for movement in said annular recess and engageable with said lower ledge of said inner ring surface when a pulling force is exerted between said first and second bone securing means to prevent removal of said femoral head from said bearing means.

35. An implantable prosthetic joint according to claim 34; wherein said inner annular ring surface includes at least one inner annular stepped portion.

36. An implantable prosthetic joint according to claim 34; wherein said upper lock ring section has a substantially L-shaped cross-sectional configuration with a first leg constituting said sliding section and a second leg including said inner arcuate surface.

37. An implantable prosthetic joint according to claim 36; wherein said lower lock ring section has a substantially L-shaped cross-sectional configuration with a first leg always in engagement with said second leg of said upper lock ring section and a second leg engageable with said lower ledge of said insert rim to prevent removal of said femoral head from said bearing means.

38. An implantable prosthetic joint according to claim 34; wherein said second bone securing means includes a longitudinal axis therethrough, and further including means for restraining movement of said upper lock ring section in a direction transverse to said longitudinal axis within said guideway and for permitting movement of said lower lock ring section in the direction of said longitudinal axis.

39. An implantable prosthetic joint according to claim 34; wherein said split spring ring means includes spring means for biasing said lower split lock ring section into a compressed condition.

* * * * *